(12) United States Patent
Härröd

(10) Patent No.: US 8,865,923 B2
(45) Date of Patent: Oct. 21, 2014

(54) METHOD FOR SEPARATING NEUTRAL AND POLAR LIPIDS AND AN OIL RICH IN POLAR LIPIDS

(75) Inventor: Magnus Härröd, Alingsås (SE)

(73) Assignee: Swedish Oat Fiber AB, Bua (SE)

( * ) Notice: Subject to any disclaimer, the term of this patent is extended or adjusted under 35 U.S.C. 154(b) by 511 days.

(21) Appl. No.: 13/255,869

(22) PCT Filed: Mar. 10, 2010

(86) PCT No.: PCT/SE2010/000052
§ 371 (c)(1),
(2), (4) Date: Dec. 1, 2011

(87) PCT Pub. No.: WO2010/104444
PCT Pub. Date: Sep. 16, 2010

(65) Prior Publication Data
US 2012/0095198 A1    Apr. 19, 2012

Related U.S. Application Data

(60) Provisional application No. 61/159,181, filed on Mar. 11, 2009.

(30) Foreign Application Priority Data

Mar. 11, 2009 (SE) ...................... 0900318

(51) Int. Cl.
| | |
|---|---|
| *C11B 3/00* | (2006.01) |
| *C07H 15/08* | (2006.01) |
| *C11B 7/00* | (2006.01) |
| *C07H 13/06* | (2006.01) |
| *C07H 1/08* | (2006.01) |

(52) U.S. Cl.
CPC ............... *C11B 7/0083* (2013.01); *C11B 3/006* (2013.01); *C07H 13/06* (2013.01); *C11B 7/0025* (2013.01)
USPC .......... 554/207; 536/128; 536/127; 536/18.3; 536/63; 536/64; 554/8; 554/10

(58) Field of Classification Search
None
See application file for complete search history.

(56) References Cited

U.S. PATENT DOCUMENTS

| | | | |
|---|---|---|---|
| 5,026,548 A | 6/1991 | Evans et al. | |
| 5,466,782 A | 11/1995 | Rousset | |

(Continued)

FOREIGN PATENT DOCUMENTS

| | | |
|---|---|---|
| EP | 0009842 | 4/1980 |
| EP | 0371601 | 6/1990 |

(Continued)

OTHER PUBLICATIONS

Zhou, M. et al., Oat Lipids, 1999, JAOCS, vol. 76, No. 2, pp. 159-169.*

(Continued)

*Primary Examiner* — Yate K Cutliff
(74) *Attorney, Agent, or Firm* — Fish & Richardson P.C.

(57) ABSTRACT

A method for separating neutral and polar lipids from an oil of biological material, wherein the oil is fractionated using a mixture of a polar solvent comprising at least one carbon atom, water and an additional substance selected from the group consisting of: mono-, di- and oligosaccharides comprising from 3 to 10 monosaccharide units, said additional substance is present in an amount of at least 0.1 wt % calculated on the total weight of solvent, water and additional substance, to form at least two liquid fractions having different densities, wherein one fraction is rich in polar lipids and another fraction is rich in neutral lipids. An oil rich in polar lipids obtained from the method is disclosed, said oil I contains at least 40, preferably at least 50 lipid % polar lipids as calculated on the total amount of lipids in said oil and that the total amount of polar solvent and water in said oil is between 20 and 30 wt %. An oat oil containing high amounts of estolides of DGDG can further be obtained.

27 Claims, 10 Drawing Sheets

□ Light Solvent
■ Light Oil
■ Oil
▨ Insoluble
▨ Emulsion
□ Solvent
■ Heavy Solvent
■ Heavy Oil
■ Crude Oil
▨ Insoluble

(56) References Cited

U.S. PATENT DOCUMENTS

| | | | |
|---|---|---|---|
| 5,620,692 A * | 4/1997 | Potter et al. | 424/401 |
| 5,688,528 A * | 11/1997 | Carlsson et al. | 424/450 |
| 6,113,908 A * | 9/2000 | Paton et al. | 424/750 |
| 6,355,693 B1 * | 3/2002 | Herslof et al. | 516/29 |
| 2004/0266999 A1 | 12/2004 | Kuriki et al. | |
| 2005/0119475 A1 * | 6/2005 | Ishikawa et al. | 536/53 |

FOREIGN PATENT DOCUMENTS

| | | |
|---|---|---|
| EP | 1043016 A1 | 11/2000 |
| WO | WO 97/11141 | 3/1977 |
| WO | WO 88/08253 | 11/1988 |
| WO | WO 95/20943 | 8/1995 |
| WO | WO 95/20944 | 8/1995 |
| WO | WO 96/38160 | 12/1996 |
| WO | WO 97/10050 | 3/1997 |

OTHER PUBLICATIONS

Rouser, G., et al., Determinatin of Polar lipids: Quantitative Column and Thin-Layer Chromatography, 1965, Journal of the American Oil Chemists' Society, vol. 42, pp. 215-227.*

Forssell, P. et al., "Comparison of Methods for Separating Polar Lipids from Oat Oil," *Pat. Sci. Technol.*, vol. 94(9): 355-358 (1992).

International Preliminary Report on Patentability, Authorized Officer, Eva Brell, dated Apr. 18, 2011, 10 pages.

International Search Report and Written Opinion in International Application No. PCT/SE2010/000052, dated May 7, 2010, 17 pages.

Elfman-Sorjesson, and Harrod, "Analysis of Non-Polar Lipids by HPLC on a Diol Column," J. High Resol. Chromatography, 1997, 20(9):516-518.

Jee, 1995, "A new emulsifier from oat," Proc. 21st World Congress ISF, The Hague, paper 135.

Moreau et al., "The identification of mono-, di-, tri-, and tetragalactosyl-diacylglycerols and their natural estolides in oat kernels," Lipids, 2008, 43:533-548.

Schneider, "Fractionation and Purification of Lecithin," Lecithins: Sources, Manufacture & Use, B.F: Szuhaj, editor, American Oil Chemists' Society, 1989, chap 7, 26 pages.

Undeland et al., "Comparison between methods using low-toxicity solvents for the extraction of lipids from herring (*Clupea harengus*)," Food Chemistry, 1998, 61(3):355-365.

* cited by examiner

METHOD FOR SEPARATING NEUTRAL AND POLAR LIPIDS AND AN OIL RICH IN POLAR LIPIDS

CROSS-REFERENCE TO RELATED APPLICATIONS

This application is a National Stage application under 35 U.S.C. §371 and claims benefit under 35 U.S.C. §119(a) of International Application No. PCT/SE2010/000052, having an International Filing Date of Mar. 10, 2010, which claims priority to Swedish Application Serial No. 0900318-7, filed Mar. 11, 2009 and also claims the benefit of U.S. Provisional Application Ser. No. 61/159,181, filed Mar. 11, 2009. The disclosures of the prior applications are considered part of (and are incorporated by reference in) the disclosure of this application.

FIELD THE OF INVENTION

The present invention relates to a method to separate neutral lipids from polar lipids. In particular, the method is suitable to produce purified oils and polar lipids from extracts, or partially concentrated extracts, or other lipid-like fractions from cereals, grains or leaves. In addition, the method opens up extraction with polar solvents as an interesting alternative to traditional non-polar solvent extraction methods, e.g. methods using hexane. The invention further refers to an oil rich in polar lipids obtained by the method.

BACKGROUND OF THE INVENTION

Vegetable oils from different origins, e.g. soy, sunflower, rape or maize, are produced by solvent extraction, commonly hexane, followed by refining. The first step in the refining is a so-called degumming, in which the polar lipids are obtained as a precipitate after an addition of approximately 2 wt % water. The polar lipid precipitate is separated from the liquid, dried, and bleach, yielding a product named lecithin. The lecithin product contains 40-60% polar lipids, the remaining fraction being mainly neutral lipids. The lecithin fraction is typically 1 wt % of the starting oil product. Lecithin obtained from soybean oil contains typically 85 wt % phospholipids, 10 wt % glycolipids and 5 wt % other substances (Lecithins: Sources, Manufacture & Use, B. F: Szuhaj, editor, American Oil Chemists' Society, 1989, chap 7).

Polar lipids constitute an important part of the cell wall membrane of the plant material and are known to display a high surface activity, which make them interesting in a multitude of applications.

Oil from oat kernels has attracted an interest as starting material to produce natural emulsifiers in several products, for example in food, cosmetics and pharmaceutical compositions. The oil from oats is obtained through extraction with a solvent, e.g. hexane or aliphatic alcohol's, such as ethanol or iso-propanol. When ethanol is used as a solvent, more polar lipids as well as sugars are extracted from the kernel. The oat oil will then contain 10-20% polar lipids, i.e. much higher levels than oil from traditional oil seeds. In addition, the polar lipids from oats, as well as the polar lipids from other cereals such as wheat and rye, have a different composition compared to the traditional oil seeds. The levels of phospholipids are low and the levels of glycolipids, mainly galactolipids, are high. A recent publication on the composition of the polar lipids in oat can be found in Lipids (2008) 43:533-548.

As the ethanol extracted oat oil is concentrated by evaporation of ethanol, parts of the sugar are dissolved in the oil together with the remaining ethanol and water, the remaining parts of the sugar form a finely dispersed precipitate which is difficult to separate through sedimentation. Particles of starch and protein may also be present in crude extracts.

Because of the high levels of polar lipids and the presence of sugars in this type of oils, traditional refining or "degumming" methods are not feasible. Large amounts of water is required to precipitate all the polar lipids, and instead of forming a separate phase a stable emulsion is produced by the surface active polar lipids. A separation would be very tedious and costly.

Patent SE-B-417 441 describes such a method, in which polar lipids from wheat are obtained from a crude oil by the addition of water. The water can be pure, but it may also contain salt up to 4 wt %. Seven parts of water and three parts of oil formed an emulsion that could be separated into three phases, neutral lipids, a mixed oil phase and an aqueous phase, only by subjecting it to high gravitational forces during a prolonged time. The mixed oil phase contained most of the polar lipids and 50-70% water. It was claimed that this fraction had good bread-making properties.

In U.S. Pat. No. 5,466,782 wheat is extracted using warm ethanol. The plant extract is filtered warm and starch and protein are removed. When the extract is cooled to between −20° C. and +4° C. ceramides are precipitated and a powder with a high content of ceramides can be filtered off. The filtrate is evaporated and an oil with 50% triglycerides, 25% galactolipids and 25% phospholipids is achieved.

In EP1043016 wheat is extracted using warm ethanol. Water and protein are removed from the extract using kieselguhr or celite and filtration, before the extract is concentrated by distillation. The oil is fractionated by addition of an emulsifier and demonized water at 70-90° C. and during 30-60 minutes before the mixture is left for 24 h. A fraction, rich in polar lipids is achieved. This fraction is frozen, freeze dried, grinded and micronized. This extract is claimed to be useful in pharmaceutical, cosmetic and food compositions.

Separations using chromatographic methods are described in several patents, e.g. EP0009842, WO95/20943 and WO9638160. Compounds with very high purity, >95%, can be produced but the process costs are very high using these methods.

Fractionations of oat oil using different solvents have previously been described. In the patent family WO 88/08253 (EP0371601, U.S. Pat. No. 5,026,548), two methods are described to obtain an extract from oats, claimed to have a strong viscosity reducing effect on chocolate. In the first method oat is extracted with a polar solvent, the oil obtained is fractionated by the addition of methanol, resulting in a methanol phase rich in the desired lipids. In the second method oat is first treated with a non-polar solvent, followed by an extraction with polar solvents, namely ethanol or iso-propanol. The latter, polar solvent extract contains the polar lipids. The effect of reduced viscosity is ascribed to the presence of digalactosyl-diglyceride (DGDG) in oats. This compound contains one or more unsaturated hydroxyl-fatty acids that are esterified by other fatty acids of the same type.

The same research group claims later that DGDG with esterified hydroxyl-fatty acids, estolides, only exists in oats (Jee M. H. 1995, "A new emulsifier from oat", Proc. 21$^{st}$ World Congress ISF, The Hague, paper 135).

In EP-A-0 371 601 a process is described, in which oat oil is fractionated using methanol. After evaporating the methanol phase, an oily fraction remains which display surface-active properties. By adding acetone to this oily fraction a lipid precipitate was obtained. This acetone insoluble material was found to be a good emulsifier, both for oil-in-water and water-in-oil emulsions. This was demonstrated in the production of bread and margarine, as well as formation and stabilisation of aqueous foams.

In WO 97/10050 an additional method for fractionation of oat oil using methanol is described. After evaporation of the methanol extract an oily substance remains. Also in this method the oily remains were further fractionated by addition of acetone. However, in contrast to the method described in EP-A-0 371 601, the surface-active component is obtained from the acetone soluble fraction. The main component in this fraction was claimed to be DGDG. The inventors claim that the acetone insoluble fraction contains mainly hydroxyl-fatty acids. The acetone soluble fraction was found to have a good stabilising effect on water-in-oil emulsions.

In WO 97/11141 a method is described whereby a plant material, for example oat, is extracted with hexane to obtain a crude oil. The hexane-extracted crude oil is further fractionated by the addition of an alcohol and water. In the experiments when ethanol is used the water concentration is below 8 wt %. The yields of recovered polar lipid fractions were 15% and the polar lipid content was approximately 40%, of which 80% were glycolipids and of this 76% DGDG. Several oil-in-water emulsions were successfully prepared using these fractions.

These methods are all rather tedious and time-consuming since they involve several extraction-steps using several different solvents. In addition, the DGDG product is recovered in a low overall yield and in relatively low concentrations of polar lipids. Hence, the methods are poorly feasible from an economical point-of-view.

The traditional extraction methods using hexane as solvent suffers from the difficulty to remove hexane from the solid residues. This residue is mostly used as feed and in this way toxic hexane is brought into our food. Hence, there is a need for methods getting rid of toxic solvent components in the feed.

Thus, an improved method for oil extraction or separation of lipids would be advantageous and in particular a method allowing for increased yield of polar lipids, improved method to handle lipids containing high amounts of polar lipids, increased possibilities to handle sugar, increased possibility to handle insoluble residues and the method should be flexible and cost-effective.

SUMMARY AND MAIN CHARACTERISTICS OF THE INVENTION

The scope of the present invention is a method that efficiently fractionates neutral lipids and polar lipids from an oil mixture, such as a crude oil or a partially evaporated extract from a biological material containing these substances. The method has to be simple and non-costly to apply and give a high yield of material.

According to the invention there is provided a method for separating neutral and polar lipids from an oil of biological material, wherein the lipids are fractionated using a mixture of a polar solvent comprising at least one carbon atom, water and an additional substance selected from the group consisting of: mono-, di- and oligosaccharides comprising from 3 to 10 monosaccharide units, said additional substance is present in an amount of at least 0.1 wt % calculated on the total weight of solvent, water and additional substance, to form at least two liquid fractions having different densities, wherein one fraction is rich in polar lipids and another fraction is rich in neutral lipids.

In one embodiment said polar solvent is selected from the following group: alcohols, ketones, esters, ethers and mixtures thereof. Preferably said polar solvent is ethanol.

In a further embodiment said polar mixture contains up to 20% by volume of a non-polar solvent. Said non-polar solvent may be selected from the group consisting of: propane, butane and hexane.

In a still further embodiment said additional substance is sucrose.

According to one aspect of the invention said additional substance is present in an amount of at least 0.5, preferably at least 1 and more preferably at least 2 wt % calculated on the total weight of solvent, water and additional substance.

According to a further aspect said oil of biological material is derived from plants, animals or microbiological species.

According to a still further aspect the oil is derived from cereals grains or leaves. Oat is one example of a cereal from which the oil is derived.

In a further embodiment the oil is derived from soybean

In one embodiment the oil is crude, fully or partially evaporated crude oil or the oil is previously fractionated.

In a further embodiment an additional fractionation step is performed on said fraction rich in polar lipids and/or said fraction rich in neutral lipids, wherein solvent and/or water is added to the respective fraction in such a way that the concentration of solvent in the mixture is controlled to at least 50 wt %, preferably at least 58 wt %, more preferably at least 60 wt %, where wt % is calculated on the total weight of solvent, water and additional substance, wherein said mixture separates into at least two fractions: a heavier fraction rich in lipids and no or very small amounts of said additional substance and a lighter solvent fraction rich in solvent, water and said additional substance In a still further embodiment at least a part of said additional substance is derived from the oil and dissolves in the mixture of solvent and water at the fractionation of the oil. According to one aspect of the invention said mixture of solvent, water and said additional substance used for fractionating the oil contains at least 25 wt % of said solvent, where wt % is calculated on the total weight of solvent, water and additional substance.

According to a further aspect said at least two liquid fractions comprises:
  a solvent phase rich in polar lipids and displaying the lowest density, and
  an oil fraction rich in neutral lipids and displaying the highest density.

The solvent fraction rich in polar lipids may be concentrated to recover a concentrated polar lipid fraction, for example by evaporation or membrane filtration.

In one embodiment said additional fractionation step is performed on said concentrated polar lipid fraction.

In a further embodiment three liquid fractions are formed at the extraction:
  a light oil phase rich in neutral lipids and also containing solvent, water and relatively low amounts of said additional substance; said light oil phase having the lowest density,
  an intermediate phase containing solvent, water and most of said additional substance, said intermediate phase having an intermediate density
  a heavy oil fraction rich in polar lipids and also containing solvent, water and relatively low amounts of said additional substance, said heavy oil fraction having the highest density.

In a still further embodiment said heavy oil fraction contains at least 25 lipid % polar lipids.

According to one aspect of the invention at least two liquid fractions and a solid fraction are formed at the extraction:
- a light oil fraction rich in neutral lipids and also containing solvent, water and relatively low amounts of said additional substance; said light oil fraction having the lowest density,
- a heavy solvent fraction rich in polar lipids said phase also containing solvent, water and said additional substance, said heavy solvent fraction rich in polar lipids having the highest density, and
- a solid fraction between the light oil fraction and the heavy solvent fraction, said solid fraction containing proteins and starch.

According to a further aspect in addition an intermediate solvent fraction is formed containing solvent, water and most of said additional substance, said intermediate fraction having an intermediate density.

According to a still further aspect the heavy solvent fraction rich in polar lipids is mixed with additional solvent and performing said additional fractionation step on the mixture so that said mixture separates into at least two fractions: a heavier oil fraction rich in polar lipids and no or very small amounts of said additional substance and a lighter solvent fraction rich in solvent and said additional substance.

In one aspect of the invention the heavy oil fraction contains at least 25, preferably at least 40, more preferably at least 50 lipid % polar lipids as calculated on the total amount of lipids in said fraction.

The invention further refers to an oil rich in polar lipids obtained from fractionating an oil of biological material according to the method above, said oil comprising a mixture of a polar solvent comprising at least one carbon atom and water, characterized in that said oil contains at least 40, preferably at least 50 lipid % polar lipids as calculated on the total amount of lipids in said oil and that the total amount of polar solvent and water in said oil is between 20 and 30 wt %.

In one embodiment the polar solvent is ethanol and that the relationship in wt % between water and ethanol in said oil is between 30:70 and 50:50.

The invention further refers to an oat oil fractionated according to the method and containing DGDG (digalactocyl diglyceride) with two fatty acids and DGDG with more than two fatty acids (estolides) wherein the oil contains more than 50% DGDG with more than two fatty acids (estolides) as calculated on the total amount of DGDG in said oil.

In the invention described herein, the fractionation of the starting material is achieved by using a mixture of a solvent comprising at least a carbon atom, water and an additional substance, an additive chosen from the group consisting of mono-, di-, or oligosaccharide comprising 3 to 10 monosaccharide units. During the fractionation several phases may occur. The densities of the phases are controlled by controlling the concentrations of the solvent comprising at least a carbon atom, the water and the additional substance.

Good fractionation results occur in at least three different ways:

1) Two fractions
   - a light solvent phase, rich in polar lipids and said additional substance, e.g. sugar, and displaying the lowest density,
   - a dense oil fraction, rich in neutral lipids, and displaying the highest density.
   - After fractionation the light solvent phase is evaporated and if required the additional substance, e.g. sugar is removed from the oil rich in polar lipids.

2) Three fractions,
   - an oil-phase, rich in neutral lipids, and with the lowest density,
   - a solvent-phase, rich in additional substance, e.g. sugar, but almost free from lipids, with an intermediate density,
   - an oil-fraction, rich in polar lipids, and displaying the highest density.
   - After fractionation, if required, the additional substance, e.g. sugar, is removed from the oil rich in polar lipids.

3) Four phases
   - an oil-phase, rich in neutral lipids, and with the lowest density,
   - a solvent-phase, rich in additional substance, e.g. sugar, but almost free from lipids, and with a higher density,
   - solid particles of insoluble starch and protein are floating in the top of the phase above, a heavy solvent-phase, rich in polar lipids, and displaying the highest density.
   - After fractionation, the ethanol concentration of the heavy solvent phase is increased above a critical level and then a heavy oil fraction, rich in polar lipids and a light solvent phase, rich in additional substance, e.g. sugar, and almost free from lipids are formed very fast.

The ratio of solvent to water is the key parameter for the separation between neutral and polar lipids. The ratio of oil to solvent phase is very important for the yield.

The polar solvent comprising at least a carbon atom should be highly soluble in water and capable of dissolving the neutral and polar lipids, completely or to a certain part. Preferred polar solvents are methanol, ethanol, propanol and butanol. The most preferred polar solvent is ethanol.

Methods to recover and recirculate the solvent are given.

The additional substance should be highly soluble in the mixture of solvent and water and it should be selected in such a way that it impairs the emulsion stability of the system and that it controls the density of specific phases in the system. The preferred substance is sugar and the most preferred substance is sucrose. Methods to recover and recirculate the additional substance are given. Methods to fractionate the additional substance from oils are also given.

The polar lipids obtained are preferably glycolipids and/or phospholipids. The most interesting glycolipid in oat oils is digalactocyl diglyceride (DGDG).

The methods above can also be applied on oils rich in phospholipids and low in glycolipids, e.g. crude soy oils or soy lecithins.

Further embodiments of the invention are defined in the dependent claims.

The present invention has the advantage over the prior art that it allows fast and cost-effective separation of lipids, especially separation of polar and neutral lipids.

Thus, this application describe new methods to fractionate a crude oil into polar lipids and non-polar lipids and it contains new methods allowing for increased yield of polar lipids, new methods to handle lipids containing high amounts of polar lipids, new methods to handle sugar, new methods to handle insoluble residues and the methods are flexible and cost-effective.

Today non-polar solvent, mainly hexane, is used in the edible oil production. The main reason is that non-polar solvents do not extract the sugar from the plant material, and this facilitates the downstream production to a high extent. Polar solvents do extract water and sugar from the plant material and currently no efficient method is available to handle this problem.

The new technology in this application may open a new way to replace the traditional hexane extraction with a more green ethanol extraction, because it solves the problem how to handle the sugar extracted from the plant material by using polar solvents.

Table 1 presents examples of fractionation of crude oat oil using different mixtures of solvents (ethanol, methanol), water and sugar.

Table 2 presents examples of fractionation of lecithin, a material rich in phospholipids and low in galactolipids, into polar and non-polar lipids.

Figure 8:
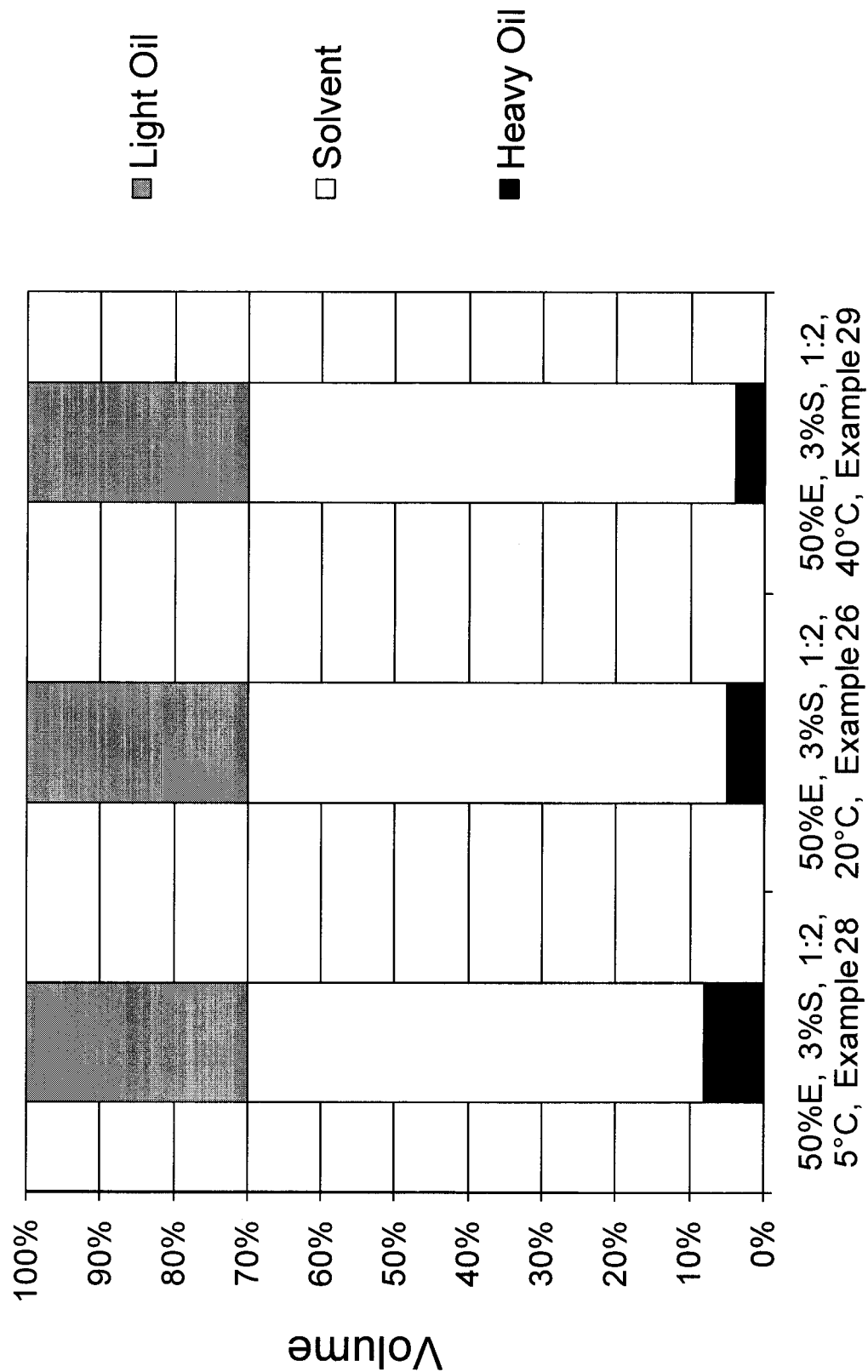

The FIGS. 2 to 10 depict the relative volume and the relative density of different phases from the Examples given in Table 1 and Table 2. The examples in the Figures are selected to demonstrate the effect on the separation due to:
Variation in solvent concentration (67-41%) at high sugar conc. (6-16%) FIG. 2.
Variation in solvent concentration (55-35%) at low sugar conc. (3%) FIG. 3.
Variation in solvent concentration (55-35%) at high sugar conc. (20%) FIG. 4.
Variation in solvent concentration (50-35%) at high sugar conc. (20%) and a large amount of solvent (the ratio of oil to solvent is 1:2) FIG. 5.
Variation in solvent concentration (51-33%) at high sugar conc. (10-18%) and a large amount of solvent (the ratio of oil to solvent range from 1:1.7 to 1:2.5) FIG. 6.
Variation in density to achieve desired separation FIG. 7.
Variation in temperature (5, 20, 40° C.) FIG. 8.
Variation in type of solvent (ethanol or methanol) FIG. 9.
Variation in type of starting material (soy lecithin instead of oat oil) FIG. 10.

Table 3 describes separation conditions, composition of the phases and yield of polar lipids using two phases (process alternative 1).

Table 4 describes separation conditions, composition of the phases and yield of polar lipids using three phases (process alternative 2).

Table 5 describes separation conditions, composition of the phases and yield of polar lipids using four phases (process alternative 3).

Table 6 contains an example describing how a fraction very rich in polar lipids can be produced and how sugar can be fractionated from oil (process alternative 4).

DETAILED DESCRIPTION OF THE INVENTION

The method of the invention is based on fractionation of oils employing a solvent comprising at least a carbon atom, water and an additional substance. During the fractionation several phases may occur. These phases should be easily separated. The densities of the phases are controlled by controlling the concentrations of the solvent comprising at least a carbon atom, the water and the additional substance. The additional substance is also used to inhibit formation of stable emulsions; in this way the separations can be performed at lower solvent concentrations without formation of stable emulsions.

Temperature can also be used to facilitate the fractionation.
Ethanol is the most preferred solvent. Sucrose is the most preferred additional substance.

The oils have a biological origin, for example of plant or animal or microbiological origin. The oils can be pressed or extracted using polar or non-polar solvents. The oils can be crude oils, fully or partially evaporated. Alternatively, the oil can be a fraction from a previous separation step.

The way the crude oil is prepared is important for the downstream processing. Below we illustrate the effect of the polarity of the extraction solvent on the quality of the crude oil using oat as starting material. However, the general trends are valid for all other plant materials and that is illustrated using soy lecithin as an example.

When oat is extracted with a non-polar solvent, e.g. hexane, it gives a crude oat oil containing lipids, no sugar, some insoluble starch and protein (1-10 wt %), very small amounts of water (0-0.5 wt %) and perhaps some traces of hexane (0-0.1 wt %). The polar lipid concentration is typically in the range 8-15% of the total lipids.

When oat is extracted with a polar solvent, e.g. ethanol, it gives a crude oat oil containing lipids, large amounts of sugar (3-15 wt %), some insoluble starch and protein (1-10 wt %), some water (3-6 wt %) and some ethanol (5-10 wt %). The solvent can not be removed further because of the sugar forming cakes impossible to handle in the evaporation equipment. The polar lipid concentration is typically in the range 12-25% of the total lipids.

The data above is intended as typical data direct after extraction and evaporation of the solvent in industrially produced oat oil. Thus there is a considerable difference if a crude oil is achieved by extraction using a non-polar solvent or a polar solvent. This must be considered in the downstream fractionation.

In the presented examples the starting material for the fractionations is crude oat oil obtained through extraction with ethanol; however, the invention includes all types of biological material containing a mixture of polar and neutral lipids, from plant species such as vegetable oils from cereal grains or leaves, or oils from animal or microbiological species.

The additional substance may be part of the biological starting material or added to the system. A preferred example of such a substance is sugar. Material from plants contains sugar and the sugar include mono-, di-, tri-, tetra- as well as oligosaccharides. As an example oat contains: monosaccharides like glucose, galactose, fructose; disaccharides like sucrose, maltose; trisaccharides like raffinose, glucodifructose, fructosan; tetrasaccharides like stachyose, pentasaccarides like verbascose. The sugar is causing both changes in the density of the phases in the system, particularly in the solvent phases, as well as reducing the emulsion stability of the system. Both these properties are desirable in the present invention. If a stable emulsion is formed the separation of phases is severely impaired. The concentration of the additional substance in the fractionation system is crucial. The additional substance may come from the plant material or it may be added from an external source. When the additional substance comes from the plant material it is primarily sugar containing a wide variety of saccharides as described for oat above. When the additional substance comes from an external source it can be pure sucrose. The additional substance should be present in an amount of at least 0.1, preferably at least 0.5, more preferably at least 1 and most preferably at least 2 wt % calculated on the total weight of solvent, water and additional substance. The maximum concentration is when the solvent/water phase becomes saturated. A simple way to estimate the max concentration of sucrose is 40% of the water content in the mixture. Besides sugar other substances may be added with similar properties, i.e. able to alter the density of the solvent phase as well as affecting the emulsion stability. The most preferred substance is sucrose.

Figure 9:
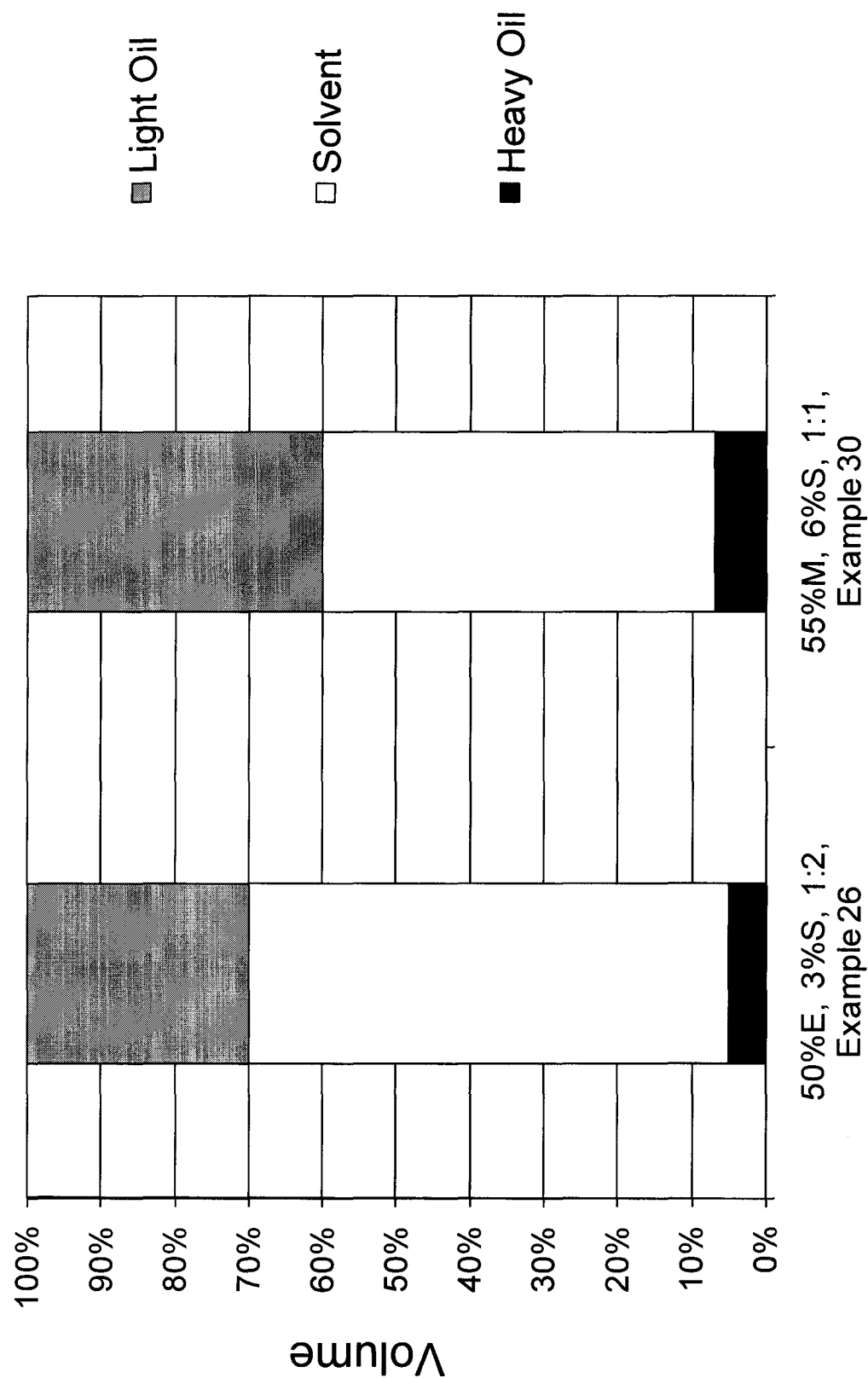
Figure 10:
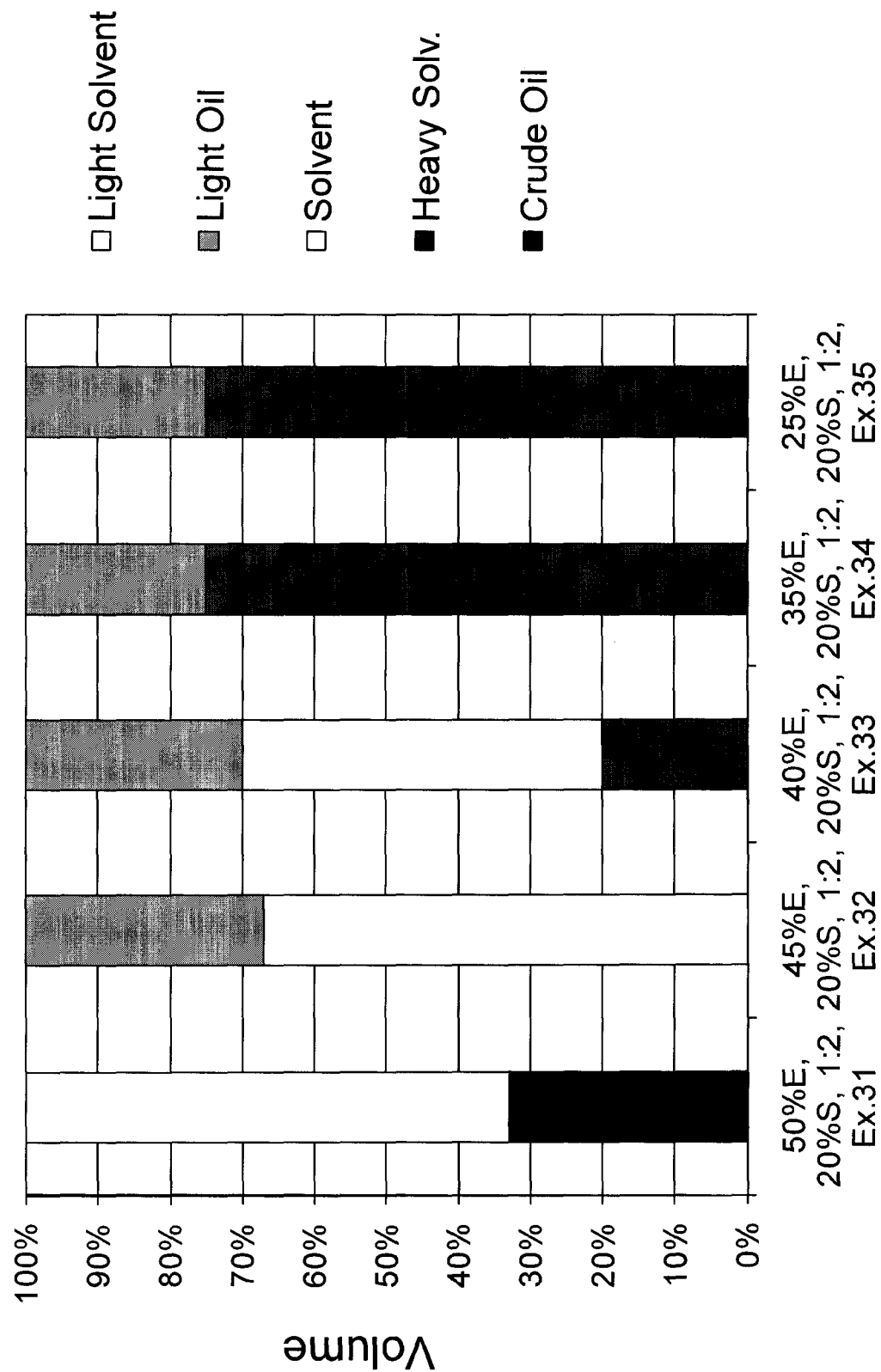

The solvent comprising at least a carbon atom, and in this text also just called solvent, is miscible with water and capable of dissolving the neutral and polar lipids, completely or to a certain degree. The preferred solvent is ethanol, but other alcohols, e.g. methanol, propanol, butanol or mixtures of these alcohols can also be used. These alcohols can also be mixed with small amounts of ketones, esters or ethers and non-polar solvents like acetone, carbon dioxide, ethyl acetate, dimethyl ether, propane, butane or hexane. If carbon dioxide, dimethyl ether, propane or butane is used, sufficient pressure must be applied. Fractionation of the starting material, consisting of a mixture of polar and neutral lipids and perhaps other components like sugar, starch and proteins, is achieved by the use of a mixture of a solvent, water and an additional substance. The fundamental pattern of phases appearing during a fractionation of an oil with polar and neutral lipids is similar for all solvents and substances. However, the exact concentrations when the different phases occur or disappear are different for different solvents and substrates. To illustrate this pattern we use mainly the system crude oat oil, ethanol, water and sucrose, see FIGS. 2-9. To illustrate that this is valid also for other oils fractionation of soy lecithin is illustrated in FIG. 10.

Good fractionation results occur in at least three different ways:
1) Two fractions
    a light solvent phase, rich in polar lipids and sugar, and displaying the lowest density,
    a dense oil fraction, rich in neutral lipids, and displaying the highest density.
    After fractionation the light solvent phase is evaporated and if required the sugar is removed from the oil rich in polar lipids.
2) Three fractions,
    an oil-phase, rich in neutral lipids, and with the lowest density,
    a solvent-phase, rich in sugar but almost free from lipids, with an intermediate density,
    an oil-fraction, rich in polar lipids, and displaying the highest density.
    After fractionation, if required, the sugar is removed from the oil rich in polar lipids.
3) Four phases
    an oil-phase, rich in neutral lipids, and with the lowest density,
    a solvent-phase, rich in sugar but almost free from lipids, and with a higher density,
    solid particles of insoluble starch and protein are floating in the top of the phase above,
    a heavy solvent-phase, rich in polar lipids, and displaying the highest density.
    After fractionation, the ethanol concentration of the heavy solvent phase is increased above a critical level and then a heavy oil fraction, rich in polar lipids and a light solvent phase, rich in sugar and almost free from lipids are formed very fast.

A good mixing before the separation should start is important, in order to achieve a good yield and a high purity of the lipid phases.

A first embodiment, (1) comprises a separation using two liquid fractions,
    After separation this embodiment results in:
    An oil fraction rich in neutral lipids, containing some solvent and water. The insoluble starch and protein will stay with the neutral lipid fraction.
    A "Light Solvent"-phase rich in solvent, water, additional substance and polar lipids.

The ratio of polar to neutral lipids in the "Light Solvent"-phase is controlled by ratio of solvent to water in the initial mixture. An oil with a polar lipid content up to 95 lipid %, i.e. concentration of polar lipids up to 95 wt % of total lipids, has been achieved; see Exp 38 in Table 3.

To achieve high yields large amounts of solvent and water is required in the initial mixture. Further, if the starting material is extracted using a polar solvent the crude oil will contain large amounts of sugar and insoluble starch and protein. The sugar will be extracted together with the polar lipids to the "Light solvent"-phase. Thus, an additional fractionation step will be required to get a polar lipid fraction low in sugar. Such a step is described in embodiment (4) below.

In summary, the "Light Solvent" phase can be used to produce an oil that contains at least 25 lipid % of polar lipids, i.e. the concentration of polar lipids is at least 25 wt % of total lipids.

A second embodiment, (2) comprises a separation with three liquid fractions.

The second embodiment, a single step fractionation, results in:
    an upper "Light Oil"-phase of clear oat oil, comprising mostly of the neutral lipids, some polar lipids, some solvent and water and a very low amount of sugar;
    an intermediate phase of "Solvent"-phase containing most of the sugar and solvent and water;
    a lower "Heavy oil"-fraction consisting of a high purity of polar lipids, some solvent and water and a very low amount of sugar;

In some cases the polar lipid concentration in the "Heavy oil" has been high, over 70 lipid %. Good yield, over 35 lipid %, has been achieved. (see Table 4). Thus, in summary this "Heavy Oil" fraction contains at least 25 lipid % of polar lipids, i.e. the concentration of polar lipids is at least 25 wt % of total lipids.

Figure 6:
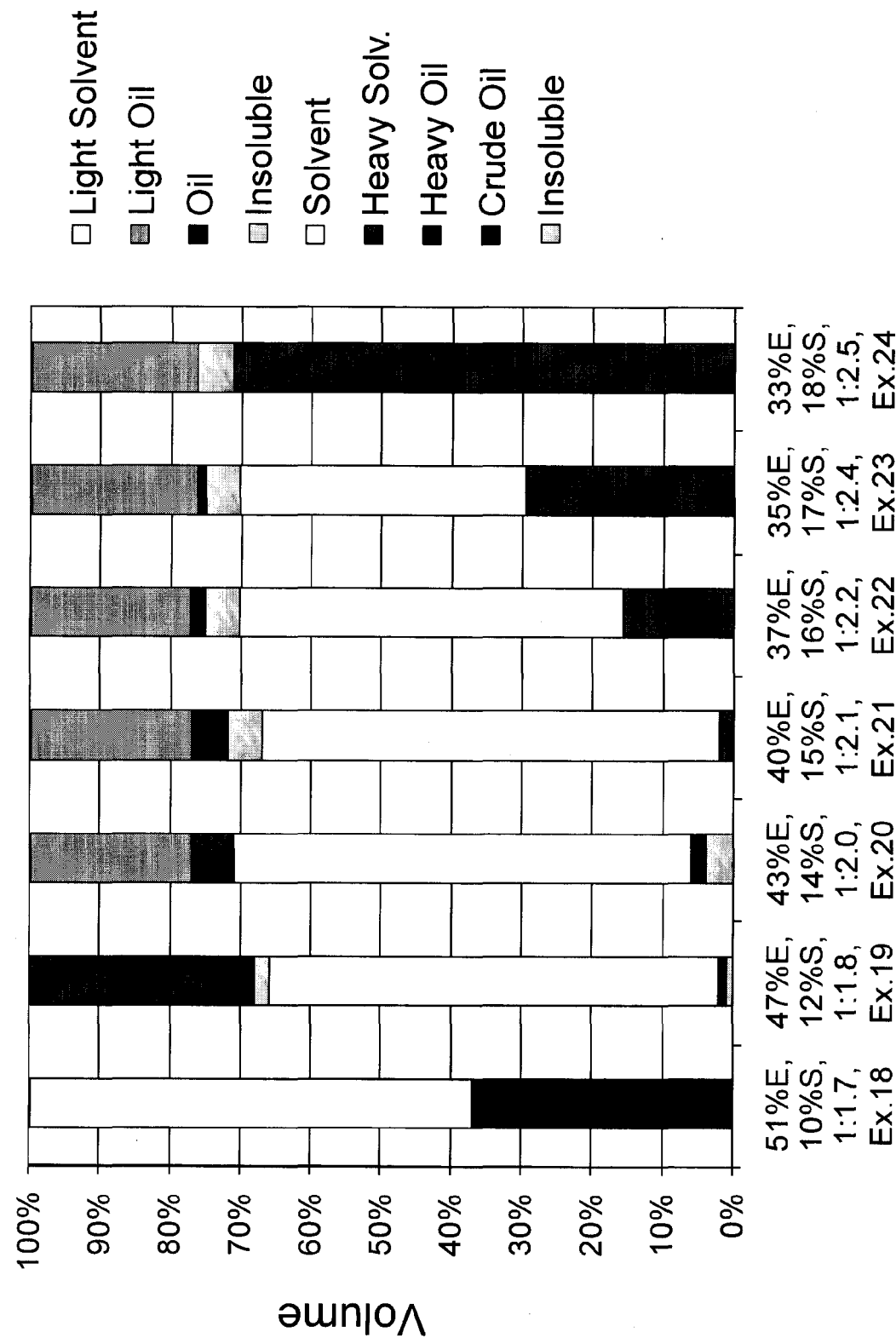
Figure 7:
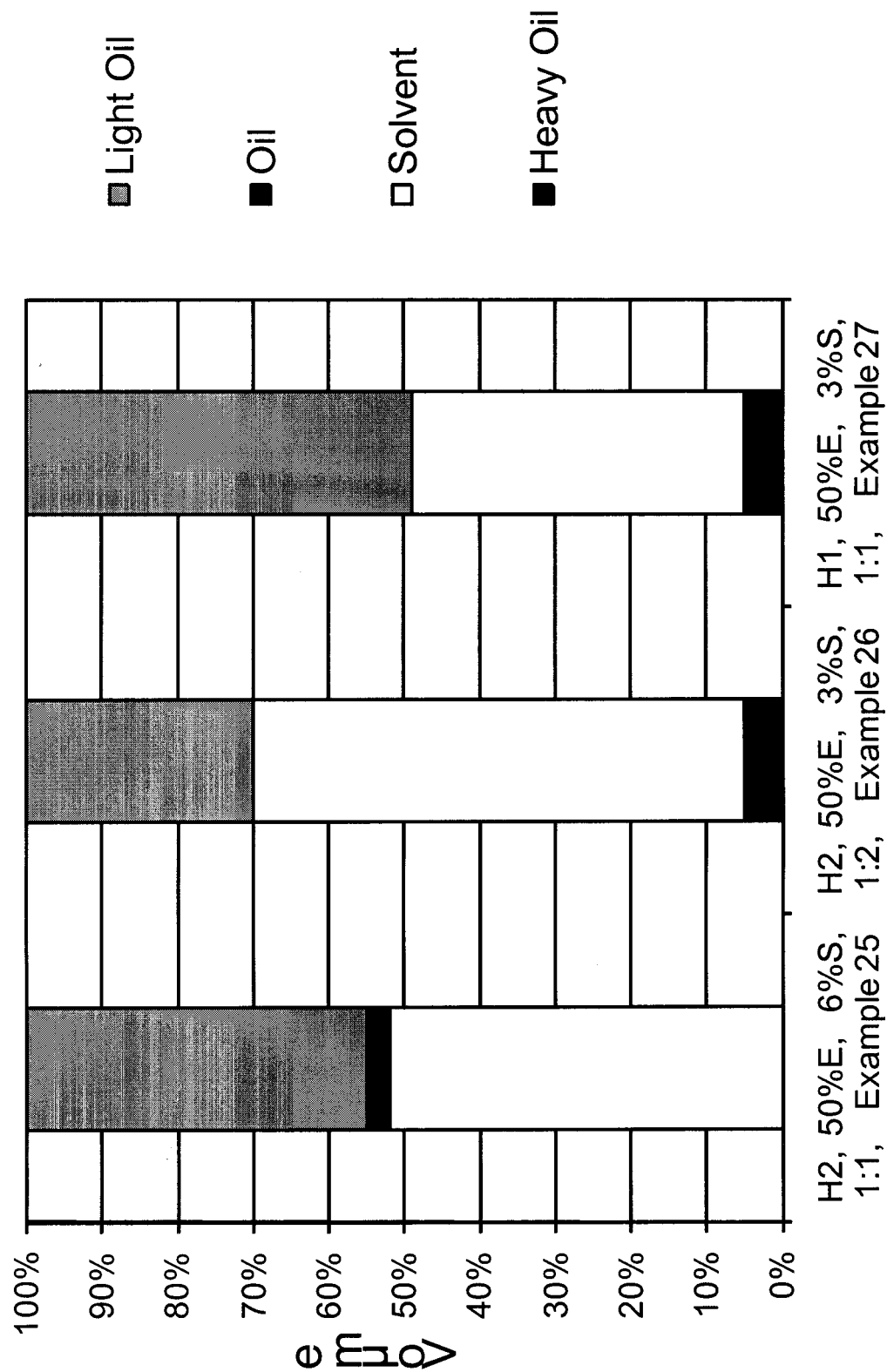

If the crude oil contains insoluble starch and protein, these compounds will come out together with the "Heavy Oil"-fraction, see Examples 19, 20 in FIG. 6.

After separation, the "Solvent"-phase can be concentrated to recover the solvent and the saccharides and then the water can be removed. The concentration method can be e.g. evaporation, distillation or membrane filtration.

A third embodiment, (3) comprises a separation with three liquid phases and a solid fourth phase.

The phase pattern is characterized by
    an oil phase, "Light Oil"-phase or a "Light Oil"-phase and an "Oil"-phase, at the top;
    an "Insoluble" solid-phase is floating in the top of the "Solvent"-phase.
    a "Solvent"-phase in the middle and
    a "Heavy Solvent"-phase in the bottom. In some cases the "Heavy Solvent"-phase fills the whole volume from the bottom to the oil phase.

After separation with this embodiment you can get:
    an upper phase of a clear oil, comprising most of the neutral lipids, small amounts of polar lipids, some solvent and water, and a very small amount of sugar;
    an intermediate fraction containing some oil from the upper phase, all insoluble starch and proteins and some solvent, water and sugar from the "Solvent"-phase or the "Heavy Solvent"-phase;
    a bottom fraction containing some "Solvent"-phase and the "Heavy Solvent"-phase. This fraction contains most of the polar lipids, a lot of sugar and a lot of solvent and water.

The ratio of volume "Solvent" to volume "Heavy Solvent", is controlled by the ratio of solvent to water. More water gives more "Heavy Solvent". If the water concentration becomes too high a stable emulsion is formed. Increased concentration of sugar allows more water in the system before a stable emulsion is formed. Thus, the mixture of solvent, water and said additional substance used for extracting the oil contains at least 25 wt % of said solvent, where wt % is calculated on the total weight of solvent, water and additional substance. The yield of polar lipids is controlled by the ratio of volume "Heavy Solvent" to volume "Oil" in the total system.

After separation, ethanol is added to the "Heavy Solvent"-phase until the ethanol concentration in the mixture reaches a critical value. For oat oils and soy lecithin this value is in the range 45 to 65 wt %. Then, a "Heavy Polar Lipid"-fraction rapidly precipitates and a "Light Solvent"-phase occurs, for details see Table 6. For a given batch of oil this transition point is very sharp and very reproducible. A change of 1 wt % in the concentration of ethanol can be enough for a complete precipitation of the "Heavy Polar Lipid"-fraction within a few minutes. We think that this transition point occurs when the polar lipids change structure from Oil-in-Water micelles to Water-in-Oil micelles.

The "Heavy Polar Lipid"-fraction can be very rich in polar lipids (over 80 lipid %, see Table 5), and a good yield of polar lipids (over 66 lipid %, see Table 5) can be achieved. Thus, in summary this "Heavy Polar Lipid" fraction contains at least 40 lipid % of polar lipids, i.e. the concentration of polar lipids is at least 40 wt % of total lipids. This fraction contains about 25 wt % of solvent and water and only small amounts of sugar, less then 1 wt %.

The "Light Solvent"-phase contains a lot of sugar and solvent but only very small amounts of lipids. The "Light Solvent"-phase can be evaporated to recover the solvent and the sugar.

This means that this embodiment is very efficient in handling crude biological oils in large scale processes.

A fourth embodiment (4)—removal of sugar from lipids and recovery of solvent. If the sugar concentration in a polar lipid fraction or in a neutral lipid fraction is too high, the sugar can be removed by extraction with an ethanol-water mixture. The solvent and/or the water can be added to the oil or to an oil fraction, in which the concentration procedure has been terminated when sufficient amount of solvent remains in the mixture.

The selectivity between sugar and oil in the fractionation is very good at an ethanol concentration of 60 wt % see Table 5 and it decreases as the ethanol concentration increases, see the ratio Lipids/Sugar in Table 3. However, if the water concentration becomes too high, stable emulsions and other unsuitable phase behaviour will occur, see e.g. FIG. 6.

Therefore, it is desirable to add solvent and/or water in such a way that the concentration of solvent in the mixture is controlled to at least 50 wt %, preferably at least 58 wt %, more preferably at least 60 wt %, where wt % is calculated on the total weight of solvent, water and additional substance, wherein said mixture separates into at least two fractions: a heavier oil fraction rich in lipids, some solvent and water, and no or very small amounts of said additional substance; and a lighter solvent fraction rich in solvent, water and said additional substance.

After separation the solvent fraction is concentrated to recover solvent and additional substance and to remove water. The concentration process may include different processes, e.g. evaporation, distillation and/or membrane filtration.

General Comments

Our experiments demonstrate that it is easier to achieve a good separation effect at a lower temperature (5° C.) than a higher temperature (20 and 40° C.). A preferred temperature can be found in the interval 0-15° C.

Separation of the phases can be achieved by natural gravitation, but is accelerated by centrifugation.

After separation the solvent fraction is concentrated to recover solvent and additional substance and to remove water. The concentration process may include different processes, e.g. evaporation, distillation and/or membrane filtration.

A Particularly Preferred Example

In a particularly preferred example of the invention the plant material is extracted with ethanol. The extract obtained contains lipids, water and saccharides. The evaporation of the ethanol and water from the extract is terminated at the point when the composition is favourable to achieve the desired separation. This may happen when the dry solid is about 30%. If necessary the concentrations of water, ethanol and saccharides are adjusted prior to the separation, which is performed through gravimetric sedimentation or by centrifugation. The fractionation can be any of the three embodiments above, however, if solid material has to be removed, embodiment 3 is the most suitable alternative.

By these four embodiments we can:
remove the insoluble starch and protein from the crude oil;
"degum" and remove sugar from the neutral lipids;
"deoiling" and remove sugar from the polar lipids;
recover and use the sugar in the starting material as a separation aid;
recover the solvent to a very high extent.

These extraction and separation processes are very favourable from both an environmental and product quality standpoint.

Production of Specific Products

"Non-Polar Oil"

When an oat oil material is processed according to the principles described in Exp 14, 16 and 24 a "Light Oil"-fraction is achieved. After separation a clear light yellow oil is achieved. The concentration of polar lipids is below 5 lipid %, the concentration of sugar is below 1 wt % and the concentration of water and ethanol is about 5 wt %, see Table 5.

"Heavy Polar Lipid"-Fraction

When an oat oil material is processed according to the principles described in Exp 14, 16 and 21-24 a "Heavy Solvent" fraction is achieved. After separation the ethanol concentration is increased above the critical value in the range 45-65 wt %, the "Heavy Polar Lipid"-fraction appears, see Table 6.

The concentration of polar lipids in this fraction is at least 40 and preferably at least 50 lipid %, the concentration sugar is as low as possible (below 2 wt %) and it contains about between 20 and 30 wt % of water and ethanol. The relationship in wt % between water and ethanol is between 30:70 and 50:50. This fraction looks basically as a dark brown clear oil. However, additional phases may appear in some cases.

Fractions "High in Estolides" and "Low in Estolides".

During different extractions and fractionations the relative composition of the different components in the polar lipids are extremely constant. In oat oil fractions the ratio of DGDG with two fatty acids to DGDG with more than two fatty acids (estolides) is close to 1.

However, we have found one exception. When the "Heavy Polar-Lipid"-fraction is treated to remove sugar, see Table 6, a "Light solvent" fraction rich in sugar is formed. In this fraction the concentration of lipids is very low. However, the lipids that occur are rich in DGDG with two fatty acids but low in estolides. This means that by treating the "Heavy Polar Lipid"- fraction with large amounts of ethanol/water like in Table 6 it is possible to produce an oil fraction rich in estolides. The concentration of polar lipids in this fraction is above 50 lipid %, the concentration sugar is below 0.1 wt % and it contains about 25 wt % of water and ethanol. The ratio of DGDG with two fatty acids to the estolides can be below 0.5. The fraction rich in estolides is particularly suitable for water in oil emulsions.

After evaporation of the "Light solvent" phase above an oil low in estolides is achieved. The concentration of polar lipids is above 75 lipid %, and the ratio of DGDG with two fatty acids to the estolides is above 2.

Experimental

Five crude oat oils (0740, 0724, H1, H2, 0845) and one partially evaporated crude oat oil fraction (M1 031) from an industrial ethanol extraction process were used as starting materials (Swedish Oat Fiber, Sua, Sweden). In addition a commercial soy lecithin has also been used as a starting material. These materials were mixed with solutions consisting of water, a solvent (ethanol or methanol) and sucrose in different ratios. The water content in the solvent was varied between 0.4 and 90%. Several volume ratios of oat oils and solvent mixtures were investigated, from 1:0.5 to 1:5. The sugar came from the crude oil and from added sugar dissolved in the solvent mixture. The samples were shaken in test tubes (total volume 5 ml or 12 ml), which were subsequently subjected to centrifugation (10 minutes at 2300 g). The separation could also be achieved at normal gravity; however, this takes in some cases several days and results in less sharp interfaces between the phases.

A few selected experiments are described in Table 1 and 2 and the resulting separations are depicted in FIGS. 2 to 10. The compositions in some of these examples are given in Tables 3-5. The lipid and sugar composition in the different phases were determined using an HPLC method as described in:

Elfman-Börjesson, I. and Härröd, M. (1997) Analysis of Non-Polar Lipids by HPLC on a Diol Column, J. High Resol. Chromatography 20(9) 516-518.

Undeland, I., Härröd, M. and Lingnert, H. (1998) Comparison between methods using low-toxicity solvents for the extraction of lipids from herring (*Clupea harengus*). Food Chemistry, 61 (3) 355-365.

Table 6 contain an experiment converting a diluted polar lipid fraction to a phase extremely high in polar lipids.

The solvent concentrations in Tables 1-6 are calculated as the volumetric concentration of the solvent in the solvent-phase in the mixtures. It is assumed that the ratio of solvent to water is the same in the solvent-phase as in the oil-phase. The solvent mixture consisted of solvent and water. The solvent was ethanol or methanol.

The sugar concentration in Table 1 and 2 is expressed as g sugar per ml of water and solvent. In the figures this unit has been abbreviated to % S. In the HPLC results the sugar concentration is defined as the weight fraction (in percent) without water and solvent, i.e. the sum of NL+GL+PL+sugar is 100% (Tables 3-6).

The sugar content of the different phases in the experiments in Table 3-6 is estimated from the relative volumes in Table 1 and concentrations received from the HPLC analysis.

Discussion

Figure 1:
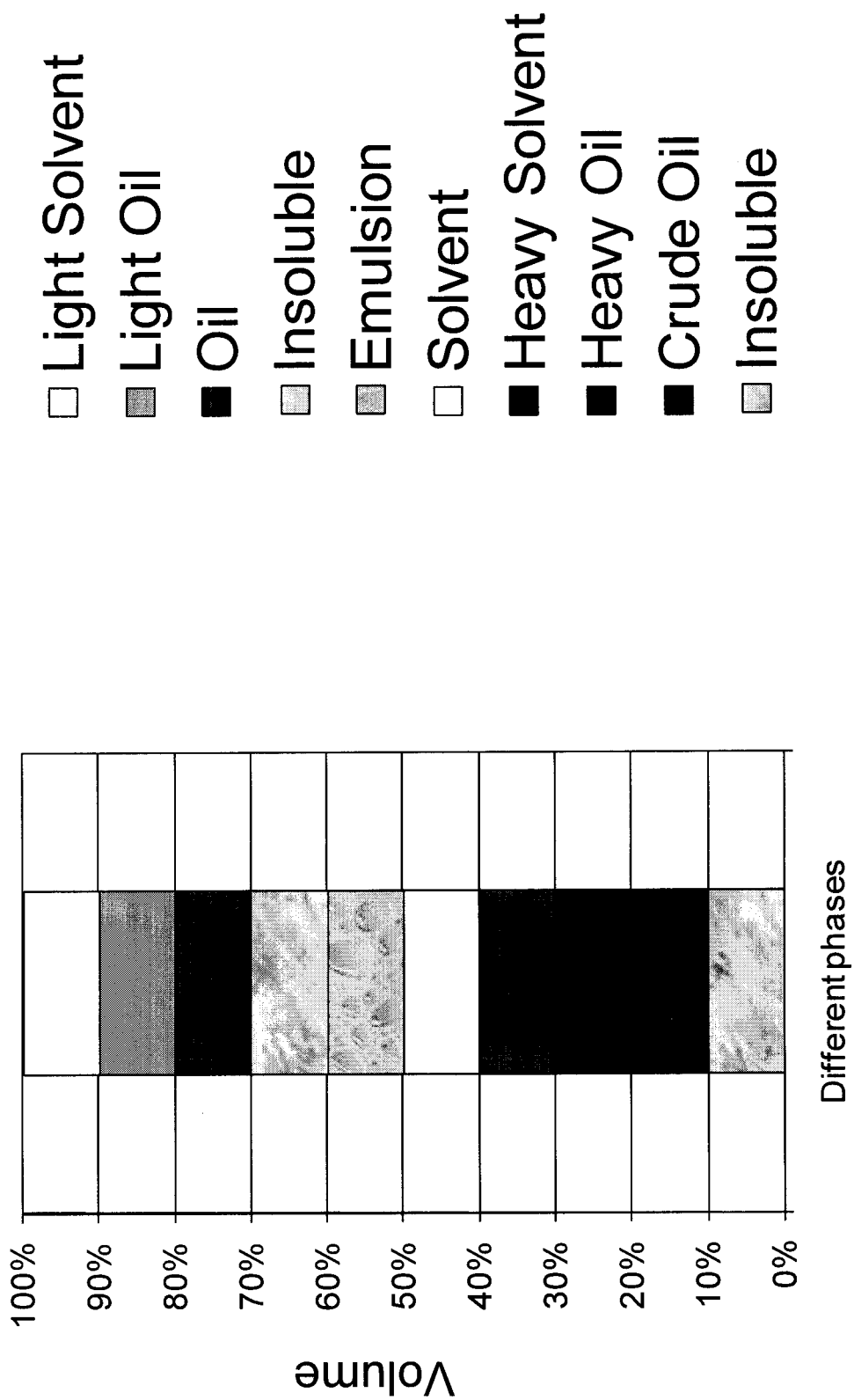
FIG. 1 illustrates different phases that may occur during fractionation of a crude oil of biological origin.

Many phases occur during fractionation of a crude oil containing neutral lipids, polar lipids, saccharides and insoluble starch and protein particles using a solvent, water and a substance. FIG. 1 illustrates these phases and their relative density.

Crude Oil

When crude oat oil is left in a storage tank, it is common that three fractions occur. In the bottom you find insoluble sugar, starch and protein. They create the densest "Insoluble"-fraction. In some cases lumps of "Heavy Polar Lipid"-phase can be found in this fraction. The "Oil"-phase is the continuous phase around the particles in the bottom. This phase is in most cases the main part of the oil. In some cases a "Light Oil" is appearing at the top of the "Oil"-phase. The "Oil"-phase has a darker colour than the "Light Oil"-phase. The polar lipid content is higher in the "Oil"-phase than in the "Light Oil"-phase. However, the difference is too small to be used for fractionation of the oil.

Emulsions

Addition of sugar is an efficient way to avoid formation of stable emulsion. When no sugar is present and the concentration of ethanol goes below 50%, stable emulsions can be formed. A stable emulsion was formed when the ethanol concentration was 45% and in this case the sugar concentration was 3%, se Exp.10 in Table 1 and FIG. 3. By increasing the sugar concentration to 18% it was possible to avoid emulsions with ethanol concentrations down to 33%, se Exp. 24 in Table 1 and FIG. 6.

No fractionation is possible when stable emulsions occur.

Solvent-Phases

At very high ethanol concentrations a "Light Solvent"-phase is floating at the top of oil fractions. The "Light Solvent"-phase is rich in polar lipids and sugar, see Table 2.

At ethanol concentrations below 57 vol % or 51%, a more dens "Solvent"-phase occurs. The "Oil"-phase and the "Light Oil"-phase has a lower density than the "Solvent"-phase, see FIG. 2-9. The "Solvent"-phase is rich in sugar and the lipid content is very low (typical below 0.2 wt %). However, almost 100% of the lipids are polar lipids in the "Solvent"-phase. See Table 4. If this phase should be utilized for fractionation the yield will be very low and from economical point of view this phase can only be used to produce very pure and very expensive fractions.

At ethanol concentrations below 45% a "Heavy Solvent"-phase starts to occur. At increasing water concentration in the mixture, this phase increases and the "Solvent"-phase decreases.

The "Heavy Solvent"-phase is rich in solvent, water, sugar and polar lipids, see FIG. 6 and Table 5.

Fractionation Using Two Phases

Fractionation according to the first embodiment, (1) Two Phases, is characterized by a "Light Solvent"-phase at the top and a "Crude Oil"-phase in the bottom. The ratio of polar lipids to neutral lipids is much higher in the "Light Solvent"-phase than in the "Crude Oil"-phase. After separation and evaporation of solvent and water from the "Light Solvent"-phase, an oil high in polar lipids and high in sugar is achieved.

Figure 2:
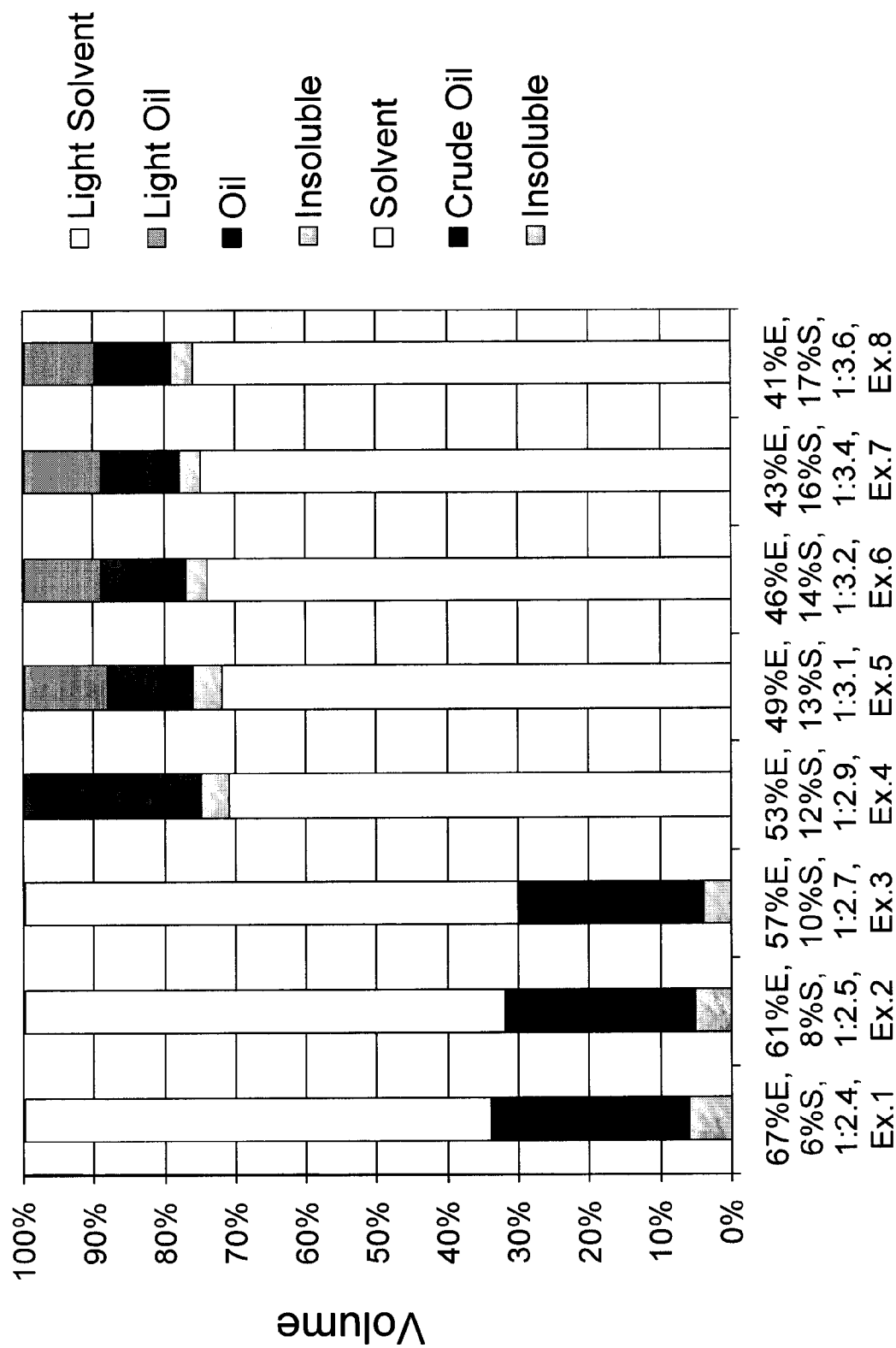
Figure 3:
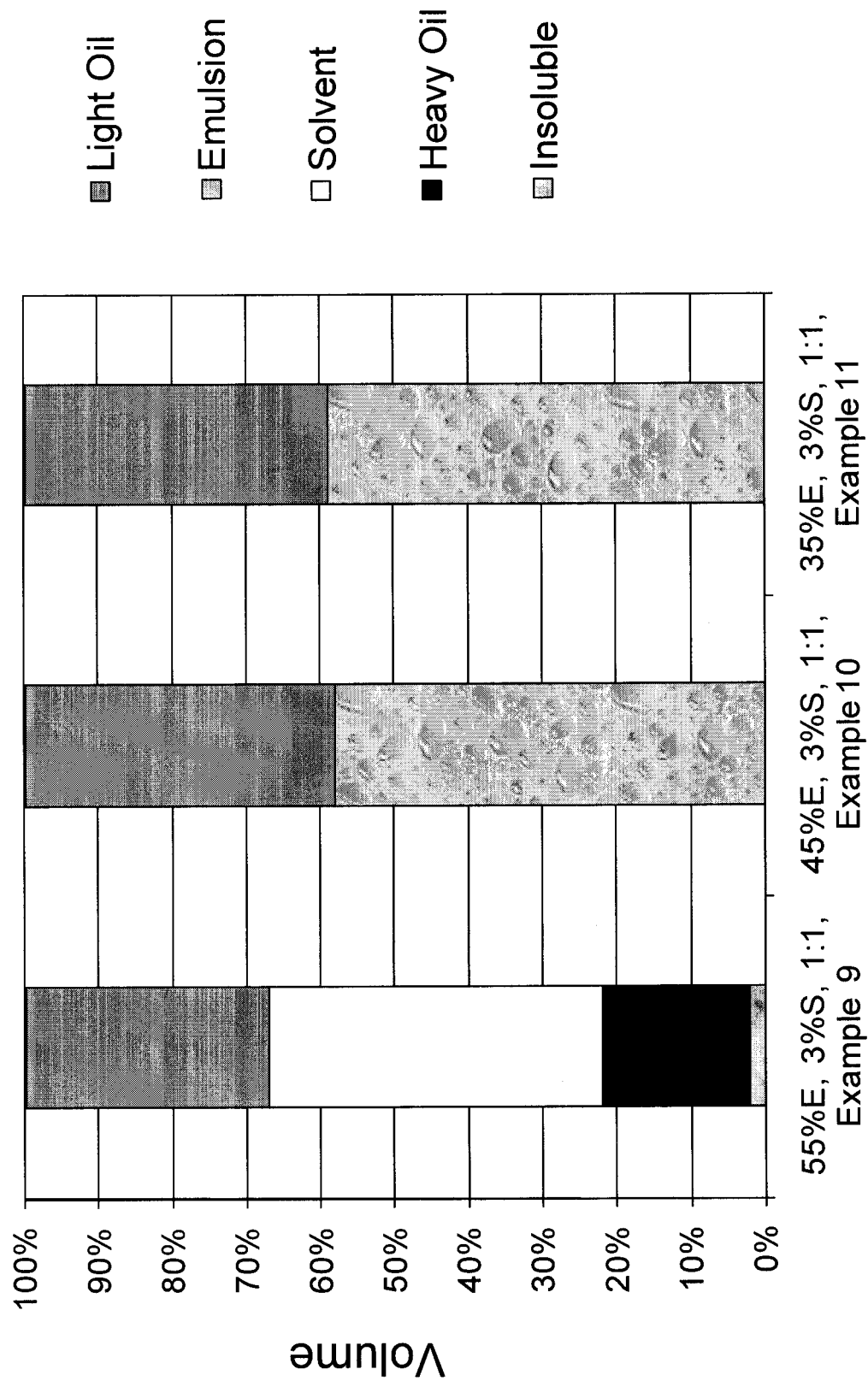
Figure 4:
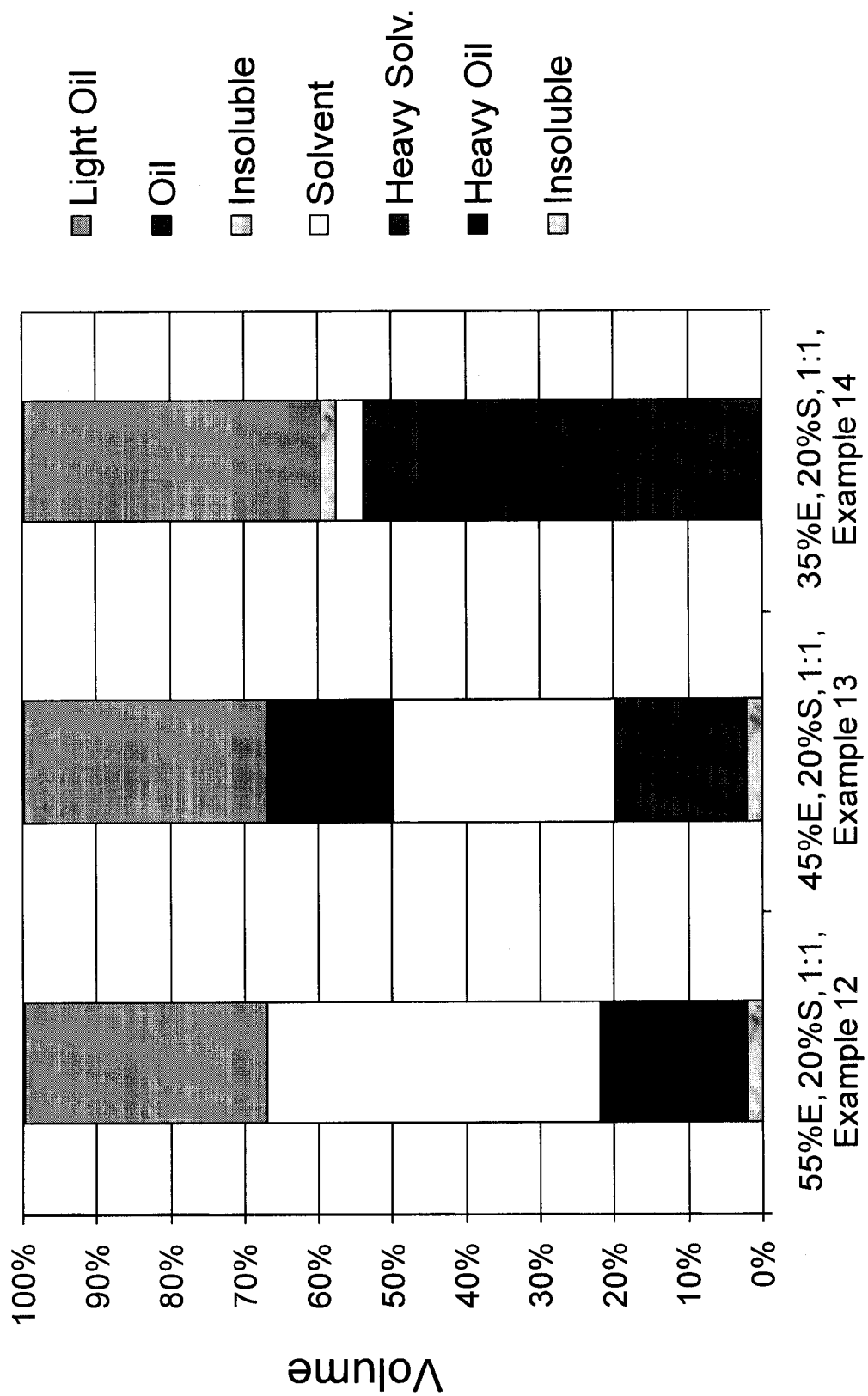
Figure 5:
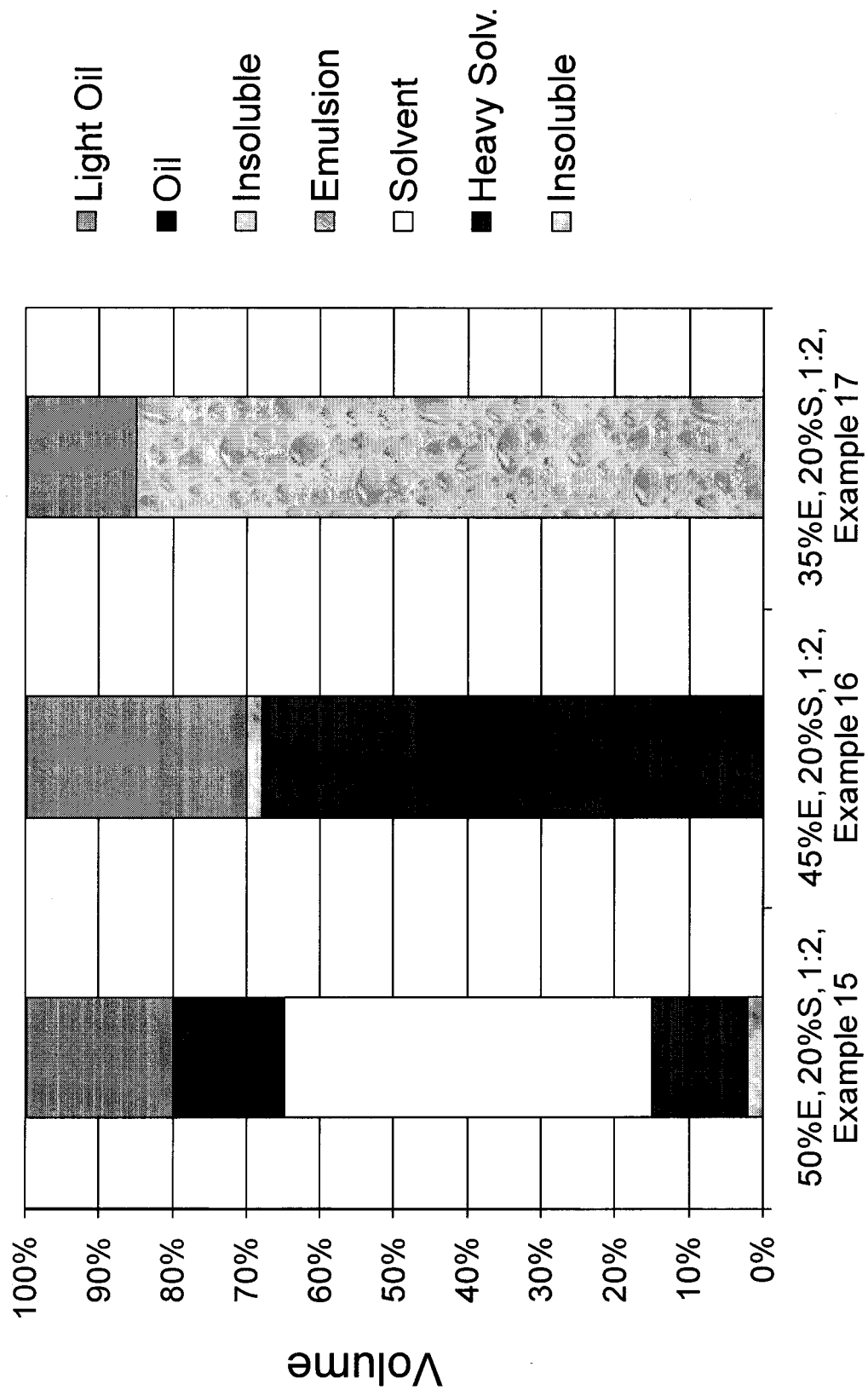

From FIG. 2 we can see that this principle can be applied as long as the ethanol concentration is above about 55 vol %. From FIG. 6 we can see that this principle can be applied as long as the ethanol concentration is above about 49 vol %. At lower ethanol content and higher water content other phases occurred and the top phase was no longer the "Light solvent" phase. In both these cases, the sugar concentration was 10%. At lower sugar content, stable emulsions may appear at these conditions and in this way prevent fractionations.

This phase behavior is illustrated in Examples 1-3 in Table 1 and FIG. 2; Example 18 in Table 1 and FIG. 6; and Examples 36-38 in Table 3. Not that the crude oat oil is derived from the oat using a polar solvent, i.e. ethanol. The sugar content is about 10%, see Tab 3.

The quality of the fractionation using this first embodiment is illustrated in Table 3. When we added 99% ethanol to the crude oat oil at a ratio 1 to 1, we got a "Light solvent" phase with a polar lipid concentration of 49%, see Exp 36 in Table 3. At increasing water content to 30% in the added solvent the concentration of polar lipid increased in the "Light solvent" phase to 96%, see Exp 36, 37, 38 in Table 3.

The yield of polar lipids was in the range of 20 to 35%, see Table 3. The yield can easily be improved by increasing the ratio of "Light solvent" to "Crude oil".

After separation and evaporation of the "Light solvent" phase we got an oil fraction high in polar lipids and very high in sugar, about 30% in exp 36 and 50% in exp 38. These concentrations of sugar must be reduced. This can be done by a fractionation step using ethanol and water at an ethanol concentration of about 60%, see Table 6.

Restrictions in Using Fractionation with Two Phases (Embodiment 1) and their Solutions.

If the heat treatment during evaporation is considered as a problem for the quality of the polar lipids, other concentration methods can be used, e.g. ultra filtration or you can use the fractionation embodiments 2 or 3 described below in this document.

If the content of sugar and/or insoluble starch and protein in the remaining "Crude oil" is considered as a problem you can use the fractionation embodiments 2 or 3 described below in this document.

A Comparison with WO97/11141

In WO 97/11141 a method is described whereby a plant material, for example oat, is extracted with a non-polar solvent to obtain a crude oil. The hexane-extracted crude oil is further fractionated by the addition of an alcohol and water.

A non-polar solvent extracts neither water nor sugar from a plant material. This means firstly that it is not possible to go as high in water content during a fractionation process as in a system containing sugar, due to the risk of formation of stable emulsions. In the examples WO 97/11141 does not present any data for more than 8 wt % water using ethanol in the fractionation process. Secondly, as the non-polar solvent does not extract any sugar they do not have to take care of any sugar in the polar lipid fraction.

Thus the presented method in WO97/11141 does not work for crude plant oils extracted with polar solvents.

Fractionation Using Three Phases

The second fractionation method, (2) Three Phases, is characterized by: a "Light Oil"-phase at the top; a "Solvent"-phase in the middle; and a "Heavy Oil"-phase in the bottom. In some cases an "Insoluble"-phase is found in the bottom together with the "Heavy Oil"-phase. After separation three phases are achieved: a phase with pure neutral lipids; a phase rich in polar lipids, however, insoluble material may occur in this phase; and a solvent phase rich in sugar but very poor in lipids.

Ethanol, water and sugar can be recovered from the solvent phase by evaporation and distillation.

This pattern may occur when the ethanol concentration is in the range 55-43%, see Examples 9, 12, 19, 20, 25-29 in Table 1 and FIGS. 3,4,6,7,8.

The crude oil H1 gives a good separation (Example 27, FIG. 7) whilst crude oil H2 gives a poor separation (Example 25, FIG. 7) at apparently the same conditions (50% E, 1:1). To obtain a good separation with crude oil H2, it was necessary to increase the solvent volume from 1:1 to 1:2 (Example 26, FIG. 7). The difference between the oils is that H1 contains approximately twice as much sugar as H2. (see total sugar concentration in Table 4, Examples 26 and 27, respectively).

Another difference is that H2 contain much more polar lipids than H1 (23 vs 17% see Table 4).

These examples (Ex 25, 26, and 27 in Table 1 and FIG. 7) demonstrate that by adjusting the ethanol concentration and sugar concentration, the density of the "Solvent"-phase can be controlled so that its density is between the densities of the "Oil"-phase and the "Heavy Oil"-phase.

The effect of varying the temperature on the separation is illustrated in FIG. 8, Examples 28, 26, 29 (5, 20, and 40° C.). A lower temperature results in a higher overall yield (35%) and higher concentration (70%) of polar lipids in the heavy oil fraction (compare Example 28 with Examples 26 and 29 in Table 4).

Methanol as Solvent

Similar separation can also be achieved using other solvents. FIG. 9 demonstrates a successful separation using methanol as solvent. The water concentration used is slightly lower with methanol than ethanol as solvent. Both the difference in density between ethanol and methanol, as well as the different polarity between the solvents (compare Example 26 and 30 in FIG. 9) can explain this. Under these conditions the composition of the phases using methanol in the separation is about the same as the phases in the ethanol based separation at 5° C. (compare Examples 30 and 28 in Table 4).

Restrictions in Using Fractionation with Three Phases (Embodiment 2) and their Solutions.

The yield of polar lipids was in the range of 4 to 35% at a ratio of oil to solvent of 1:2. This indicates that the embodiment is sensitive to actual process conditions and variations in crude oil. Embodiments 1 and 3 give both a more robust process.

If the "Crude oil" contains insoluble material, this material is found in the fraction high in polar lipids. If this is a problem, use embodiments 1 or 3.

Fractionation Using Four Phases

The fractionation using four phases, embodiment (3), is characterized by: a "Light Oil"-phase at the top; a "Solvent"-phase in the middle; the "Insoluble" materiel is floating in the top of the "Solvent"-phase and; a "Heavy Solvent"-phase in the bottom. This fractionation pattern can be found for oat oils in Examples 14, 21-23, see Table 1 and FIGS. 4,6. and for soy lecithin in Examples 31-35, see Table 2 and FIG. 10. In some cases the "Heavy Solvent"-phase fills the whole volume under the "Light Oil"-phase. In this case the "Insoluble" material is floating in the top of the "Heavy Solvent"-phase. This fractionation pattern can be found for oat oils in Examples 16, 24, see Table 1 and FIGS. 5, 6 and for soy lecithin in Examples 34, 35, see Table 2 and FIG. 10.

After fractionation the "Heavy Solvent" phase is further fractionated into a "Light Solvent" phase and a "Heavy PL" phase by increasing the ethanol concentration above a critical concentration of ethanol in the range 45 to 65 wt %., see Table 6.

FIG. 6 gives a good view of the fractionation mechanism. At high concentration of ethanol, Ex.21, the "Heavy Solvent"-phase is small and the "Oil"-phase is large. More water in the system, see Ex.22-24, reduces the volume of the "Oil"-phase and increases the "Heavy Solvent"-phase, i.e. the water extracts the polar lipids from the "Oil"-phase to the "Heavy Solvent"-phase. To achieve maximal yield it is important to have a large ratio of solvent to oil and a lot of sugar in the system to avoid formation of stable emulsions.

Since it is desirable to get a "Heavy Solvent" and a "Light Oil" without any "Insoluble" material, three fractions are achieved after a good separation: pure "Heavy Solvent"; pure "Light Oil"; and "Insoluble" with some "Solvent" or "Heavy Solvent" and some "Light Oil".

The composition of the phases achieved during the fractionation in Exp.24 is given in Table 5. The composition of the "Light Oil" is: neutral lipids (95% of lipids), polar lipids (5% of lipids), sugar (<1 wt %) and solvent+water (5 wt %).

The "Heavy Solvent" contains 66% of the polar lipids a lot of solvent and sugar, see Table 5

Therefore, the "Heavy Solvent" is further processed; see Example 39 in Table 6. The concentration of ethanol is increased to about 60% by addition of a fraction rich in ethanol, e.g. 92% ethanol. Then, a "Heavy PL" and a "Light Solvent" phase are almost completely developed within a few minutes. The "Heavy PL" is very heavy and it contains almost all the lipids. The composition of the "Heavy PL" can be: neutral lipids (20% of lipids), polar lipids (80% of lipids), sugar (<1 wt %) and solvent+water (20 wt %), see Table 6. Similar data were achieved using soy lecithin as starting material.

Polar lipids with very high quality are achieved using this embodiment due to the very low heat treatment required.

The "Light Solvent"-phase contains almost no lipids. After separation, the "Light Solvent"-phase can be evaporated and distilled to recover the ethanol and to remove the water. The sugar can be circulated back to the initial step of the fractionation process.

Pros Using Fractionation with Four Phases (Embodiment 3)

The crude oil is fractionated into four fractions characterized by:

An oil very high in polar lipids, almost no sugar, no insoluble material, and very low heat treatment.

An oil low in polar lipids, almost no sugar, no insoluble material, and very low heat treatment.

A liquid fraction very high in sugar, low in lipids, no insoluble material.

A small liquid fraction containing all the insoluble material.

A robust process with a very high degree of separation is achieved.

TABLE 1

Fractionation of different Oat oils using different solvents, temperatures and concentrations of water, solvent and sugar

| | | solvent mixture | | | ratio | | | | | Fraction | | | | | | |
| | | | | | | | crude | heavy | heavy | | | | | | light | light |
| Exp no | oil batch | solv. type | solv. vol % | sugar g/ml | mix:oil vol/vol | temp °C | insol. vol % | oil vol % | oil vol % | solv. vol % | solv. vol % | emul. vol % | insol. vol % | oil vol % | oil vol % | solv. vol % |
|---|---|---|---|---|---|---|---|---|---|---|---|---|---|---|---|---|
| 1 | 07 40 | EtOH | 67 | 6 | 2.4 | 22 | 6 | 28 | | | | | | | | 66 |
| 2 | 07 40 | EtOH | 61 | 8 | 2.5 | 22 | 5 | 27 | | | | | | | | 68 |
| 3 | 07 40 | EtOH | 56 | 10 | 2.7 | 22 | 4 | | | | | | | | | 70 |
| 4 | 07 40 | EtOH | 53 | 12 | 2.9 | 22 | | | | | 71 | | 4 | 25 | | |
| 5 | 07 40 | EtOH | 49 | 13 | 3.1 | 22 | | | | | 72 | | 4 | 12 | 12 | |
| 6 | 07 40 | EtOH | 46 | 14 | 3.2 | 22 | | | | | 74 | | 3 | 12 | 11 | |
| 7 | 07 40 | EtOH | 43 | 16 | 3.4 | 22 | | | | | 75 | | 3 | 11 | 11 | |
| 8 | 07 40 | EtOH | 41 | 17 | 3.6 | 22 | | | | | 76 | | 3 | 11 | 10 | |
| 9 | 07 24 | EtOH | 55 | 3 | 1 | 22 | 2 | 20 | | | 45 | | | | 33 | |
| 10 | 07 24 | EtOH | 45 | 3 | 1 | 22 | | | | | | 58 | | | 42 | |
| 11 | 07 24 | EtOH | 35 | 3 | 1 | 22 | | | | | | 59 | | | 41 | |
| 12 | 07 24 | EtOH | 55 | 20 | 1 | 22 | 2 | 20 | | | 45 | | | | 33 | |
| 13 | 07 24 | EtOH | 45 | 20 | 1 | 22 | 2 | | | 18 | 30 | | | 17 | 33 | |
| 14 | 07 24 | EtOH | 35 | 20 | 1 | 22 | | | | 56 | 4 | | 2 | | 42 | |
| 15 | 07 24 | EtOH | 35 | 20 | 2 | 22 | 2 | | | 13 | 50 | | | 15 | 20 | |
| 16 | 07 24 | EtOH | 45 | 20 | 2 | 22 | | | | | 68 | | 2 | | 30 | |
| 17 | 07 24 | EtOH | 50 | 20 | 2 | 22 | | | | | | 85 | | | 15 | |
| 18 | M1031 | EtOH | 51 | 10 | 1.7 | 22 | 37 | | | | | | | | | 63 |
| 19 | M1031 | EtOH | 47 | 12 | 1.8 | 22 | 1 | | 1 | | 64 | | 2 | 31 | | |
| 20 | M1031 | EtOH | 43 | 13 | 2.0 | 22 | 4 | | 2 | | 65 | | | 6 | 23 | |
| 21 | M1031 | EtOH | 40 | 15 | 2.1 | 22 | | | 2 | | 65 | | 5 | 5 | 23 | |
| 22 | M1031 | EtOH | 37 | 16 | 2.2 | 22 | | | | 16 | 55 | | 5 | 2 | 23 | |
| 23 | M1031 | EtOH | 35 | 17 | 2.4 | 22 | | | | 30 | 41 | | 5 | 1 | 24 | |
| 24 | M1031 | EtOH | 33 | 18 | 2.5 | 22 | | | | | 72 | | 5 | | 24 | |
| 25 | H2 | EtOH | 50 | 6 | 1 | 20 | | | | | 52 | | | 3 | 45 | |
| 26 | H2 | EtOH | 50 | 3 | 2 | 20 | | 5 | | | 65 | | | | 30 | |
| 27 | H1 | EtOH | 50 | 3 | 1 | 20 | | 5 | | | 44 | | | | 51 | |
| 28 | H2 | EtOH | 50 | 3 | 2 | 5 | | 8 | | | 62 | | | | 30 | |
| 26 | H2 | EtOH | 50 | 3 | 2 | 20 | | 5 | | | 65 | | | | 30 | |
| 29 | H2 | EtOH | 50 | 3 | 2 | 40 | | 4 | | | 66 | | | | 30 | |
| 26 | H2 | EtOH | 50 | 3 | 2 | 20 | | 5 | | | 65 | | | | 30 | |
| 30 | H2 | MeOH | 55 | 6 | 1 | 20 | | 7 | | | 53 | | | | 40 | |

TABLE 2

Fractionation of Lecithin using different concentrations of water, ethanol and sugar

| | | solvent mixture | | | ratio | | Fraction | | | | | | | | | |
|---|---|---|---|---|---|---|---|---|---|---|---|---|---|---|---|---|
| | | | | | | | crude | heavy | heavy | | | | | light | light | |
| Exp no | oil batch | solv. type | solv. vol % | sugar g/ml | mix:oil vol/vol | temp °C. | insol. vol % | oil vol % | oil vol % | solv. vol % | solv. vol % | emul. vol % | Insol. vol % | oil vol % | oil vol % | solv. vol % |
| 31 | Lecithin | EtOH | 50 | 20 | 2 | 22 | 33 | | | | | | | | | 67 |
| 32 | Lecithin | EtOH | 45 | 20 | 2 | 22 | | | | 67 | | | | 33 | | |
| 33 | Lecithin | EtOH | 40 | 20 | 2 | 22 | | | 20 | 50 | | | | 30 | | |
| 34 | Lecithin | EtOH | 35 | 20 | 2 | 22 | | | 75 | | | | | 25 | | |
| 35 | Lecithin | EtOH | 25 | 20 | 2 | 22 | | | 75 | | | | | 25 | | |

TABLE 3

Composition of some fractions during fractionation type (1)

| | | | | Composition | | | | | | |
|---|---|---|---|---|---|---|---|---|---|---|
| | Separation | | Phases | Lipids | | | | Polar Lipids | | |
| Exp. no | EtOH % | vol:vol | volume parts | NL parts | PL parts | Sugar parts | Insol. parts | conc % lipid | yield % | Lipids/sugar ratio |
| 36 | | | Light solv 1 | 47 | 45 | 50 | 0 | 48.9 | 23.1 | 1.84 |
|    | | | Crude oil 1 | 950 | 150 | 80 | na | 13.6 | | 13.75 |
|    | 99 | | | 997 | 195 | 130 | | 16.4 | | 9.17 |
| 37 | | | Light solv 1 | 15 | 42 | 75 | 0 | 73.5 | 19.6 | 0.75 |
|    | | | Crude oil 1 | 950 | 170 | 45 | na | 15.2 | | 24.89 |
|    | 92 | | | 965 | 212 | 120 | | 18.0 | | 9.80 |
| 38 | | | Light solv 1 | 1 | 28 | 28 | 0 | 96.2 | 35.5 | 1.04 |
|    | | | Crude oil 1 | 300 | 50 | 12 | na | 14.3 | | 30.00 |
|    | 70 | | | 301 | 78 | 39 | | 20.5 | | 9.67 |

TABLE 4

Separation conditions type (2), Composition of the phases and yield of the polar lipids.

| | | Separation conditions | | | | | Composition | | | | | Polar lipids | |
|---|---|---|---|---|---|---|---|---|---|---|---|---|---|
| Exp. no. | Oil [1)] batch | Solvent mixture [2)] solv | Oil/solv vol % [3)] | vol/vol | Temp °C. | Phases | NL [4)] wt % | GL [5)] wt % | PhL [6)] wt % | Sugar [7)] wt % | TOTAL wt % | Conc. [8)] wt % | Yield [9)] wt % |
| 28 | H2 | EtOH | 50 | 1:2 | 5 | Oil | 68.54 | 10.39 | 2.35 | 1.91 | 83 | 16 | — |
| | | | | | | Solvent | 0.00 | 0.03 | 0.00 | 5.34 | 5 | 100 | 0.2 |
| | | | | | | Heavy oil | 2.97 | 5.02 | 1.95 | 1.50 | 11 | 70 | 35 |
| | | | | | | Total | 71.51 | 15.44 | 4.30 | 8.75 | 100 | 22 | — |
| 26 | H2 | EtOH | 50 | 1:2 | 20 | Oil | 64.41 | 18.55 | 3.69 | 2.67 | 89 | 26 | — |
| | | | | | | Solvent | 0.04 | 0.07 | 0.00 | 7.21 | 7 | 67 | 0.3 |
| | | | | | | Heavy oil | 2.31 | 0.70 | 0.15 | 0.21 | 3 | 27 | 4 |
| | | | | | | Total | 66.75 | 19.32 | 3.84 | 10.09 | 100 | 26 | — |
| 29 | H2 | EtOH | 50 | 1:2 | 40 | Oil | 65.58 | 15.50 | 3.47 | 2.93 | 87 | 22 | — |
| | | | | | | Solvent | 0.03 | 0.13 | 0.00 | 8.20 | 8 | 83 | 0.6 |
| | | | | | | Heavy oil | 2.65 | 1.04 | 0.25 | 0.22 | 7 | 33 | 6 |
| | | | | | | Total | 68.25 | 16.68 | 3.72 | 11.35 | 100 | 23 | — |
| 27 | H1 | EtOH | 50 | 1:1 | 20 | Oil | 78.54 | 10.51 | 2.69 | 2.30 | 97 | 14 | — |
| | | | | | | Solvent | 0.01 | 0.14 | 0.00 | 2.42 | 3 | 91 | 0.9 |
| | | | | | | Heavy oil | 0.51 | 1.82 | 0.59 | 0.47 | 3 | 83 | 15 |
| | | | | | | Total | 79.06 | 12.47 | 3.28 | 5.19 | 100 | 17 | — |

TABLE 4-continued

Separation conditions type (2), Composition of the phases and yield of the polar lipids.

| Exp. no. | Oil[1] batch | Solvent mixture[2] solv | Oil/solv vol %[3] | Temp vol/vol | °C. | Phases | NL[4] wt % | GL[5] wt % | PhL[6] wt % | Sugar[7] wt % | TOTAL wt % | Conc.[8] wt % | Yield[9] wt % |
|---|---|---|---|---|---|---|---|---|---|---|---|---|---|
| 30 | H2 | MeOH | 55 | 1:1 | 20 | Oil | 65.47 | 12.40 | 2.83 | 2.03 | 83 | 19 | — |
|  |  |  |  |  |  | Solvent | 0.07 | 0.19 | 0.00 | 6.84 | 7 | 74 | 0.9 |
|  |  |  |  |  |  | Heavy oil | 3.23 | 4.45 | 1.34 | 1.14 | 10 | 64 | 27 |
|  |  |  |  |  |  | Total | 68.77 | 17.04 | 4.17 | 10.02 | 100 | 24 | — |

[1] Oat oil 1 (H1) or oat oil 2 (H2)
[2] Solvent and water
[3] Vol % of solvent
[4] Neutral lipids
[5] Glycolipids,
[6] Phospholipids
[7] mono, di, tri and oligosaccharides
[8] (GL + PhL)/(NL + GL + PhL) in each separate phase
[9] (GL + PhL in each phase)/(GL + PhL in total sample)

TABLE 5

Composition of some phases during fractionation type (3)

| Exp no | Separation EtOH % | vol:vol | Phases | volume parts | solvent + water EtOH parts | Water parts | NL parts | PL parts | Sugar parts | Insol. parts | Polar Lipids conc % lipid | yield % |
|---|---|---|---|---|---|---|---|---|---|---|---|---|
| 24 |  |  | Light Oil | 24 | 0.4 | 0.8 | 21.5 | 1.1 | 0.2 | 0.0 | 5 | 31 |
|  |  |  | Insoluble | 5 | 0.8 | 1.6 | 0.0 | 0.1 | 0.2 | 2.2 | 80 | 3 |
|  |  |  | Heavy Solvent | 71 | 20.6 | 41.2 | 0.6 | 2.4 | 6.2 | 0.0 | 80 | 66 |
|  | 33 | 1:2 | total | 100 | 21.8 | 43.6 | 22.1 | 3.6 | 6.6 | 2.2 | 14 |  |

TABLE 6

Composition of some phases during concentration of Polar Lipids from "Heavy Solvent" to "Heavy Polar Lipids" and removal of sugar from an oil.

| Exp no | Separation EtOH % | vol:vol | Phases | volume parts | solvent + water EtOH parts | Water parts | NL parts | PL parts | Sugar parts | Insol. parts | Polar Lipids conc % lipid | yield % | Lipids/sugar ratio |
|---|---|---|---|---|---|---|---|---|---|---|---|---|---|
| 39 | 33 |  | Heavy Solvent | 71 | 20.6 | 41.2 | 0.6 | 2.4 | 6.2 | 0.0 | 80 | 66 | 0.5 |
|  | 92 |  | EtOH | 50 | 46.0 | 4.0 |  |  |  |  |  |  |  |
|  | 60 |  | total | 121 | 66.6 | 45.2 | 0.6 | 2.4 | 6.2 | 0.0 |  |  |  |
|  |  |  | Light Solvent | 117 | 66.1 | 44.9 | 0.0 | 0.0 | 6.2 | 0.0 |  |  | 0.0 |
|  |  |  | Heavy PL | 4 | 0.5 | 0.3 | 0.6 | 2.4 | 0.0 | 0.0 | 80 | 100 | 100.0 |

The invention claimed is:

1. A method for separating neutral and polar lipids from an oil of biological material, wherein said method comprises:
   (a) providing said oil of biological material, and
   (b) contacting said oil of biological material with a mixture of a polar solvent to fractionate lipids from of said oil of biological material to form at least two liquid fractions having different densities, wherein one fraction is rich in polar lipids and another fraction is rich in neutral lipids, wherein said mixture of said polar solvent comprises at least one carbon atom, water, and an additional substance selected from the group consisting of: mono-, di- and oligosaccharides comprising from 3 to 10 monosaccharide units, wherein said additional substance is present in an amount of at least 0.1 wt % calculated on the total weight of solvent, water, and additional substance.

2. The method of claim 1, wherein said polar solvent is an alcohol.

3. The method of claim 2, wherein said polar solvent is ethanol.

4. The method of claim 1, wherein said mixture contains up to 20% by volume of a non-polar solvent.

5. The method of claim 4, wherein said non-polar solvent is selected from the group consisting of: propane, butane and hexane.

6. The method of claim 1, wherein said additional substance is sucrose.

7. The method of claim 1, wherein said additional substance is present in an amount of at least 0.5 wt % calculated on the total weight of solvent, water and additional substance.

8. The method of claim 1, wherein said oil of biological material is derived from plants, animals or microbiological species.

9. The method of claim 8, wherein said oil is derived from cereals, grains, or leaves.

10. The method of claim 9, wherein said oil is derived from oat.

11. The method of claim 8, wherein said oil is derived from soybean.

12. The method of claim 1, wherein said oil is crude, fully or partially evaporated crude oil or that said oil is previously fractionated.

13. The method of claim 1, wherein said method comprises performing an additional fractionation step on said fraction rich in polar lipids or said fraction rich in neutral lipids, wherein solvent or water is added to the respective fraction in such a way that the concentration of solvent in the mixture is controlled to at least 50 wt %, where wt % is calculated on the total weight of solvent, water and additional substance, wherein said mixture separates into at least (a) a first fraction rich in lipids and no or very small amounts of said additional substance and (b) a second solvent fraction rich in solvent, water and said additional substance, wherein said first fraction is heavier than said second fraction.

14. The method of claim 1, wherein at least a part of said additional substance is derived from the oil and dissolves in the mixture of solvent and water at the fractionation of the oil.

15. The method of claim 1, wherein said mixture of solvent, water and said additional substance used for fractionating the oil contains at least 25 wt % of said solvent, where wt % is calculated on the total weight of solvent, water and additional substance.

16. The method of claim 1, wherein said at least two liquid fractions comprises
 a solvent fraction rich in polar lipids and displaying the lowest density, and
 an oil fraction rich in neutral lipids and displaying the highest density.

17. The method of claim 16, wherein said method comprises concentrating the solvent fraction to recover a concentrated polar lipid fraction.

18. The method of claim 17, wherein said method comprises performing an additional fractionation step on said concentrated polar lipid fraction, wherein solvent or water is added to said concentrated polar lipid fraction in such a way that the concentration of solvent in the mixture is controlled to at least 50 wt %, where wt % is calculated on the total weight of solvent, water and additional substance, wherein said mixture separates into at least (a) a first heavier fraction rich in lipids and no or very small amounts of said additional substance and (b) a second lighter solvent fraction rich in solvent, water and said additional substance, wherein said first fraction is heavier than said second fraction.

19. The method of claim 1, wherein three liquid fractions are formed at the fractionation, wherein a first liquid fraction is a light oil phase rich in neutral lipids and containing solvent, water and relatively low amounts of said additional substance; said light oil phase having the lowest density, wherein a second liquid fraction is an intermediate phase containing solvent, water and most of said additional substance, said intermediate phase having an intermediate density, and wherein a third liquid fraction is a heavy oil fraction rich in polar lipids and containing solvent, water and relatively low amounts of said additional substance, said heavy oil fraction having the highest density.

20. The method of claim 19, wherein said heavy oil fraction contains at least 25 lipid % polar lipids.

21. The method of claim 1, wherein at least two liquid fractions and a solid fraction are formed at the fractionation, wherein a first liquid fraction is a light oil fraction rich in neutral lipids and containing solvent, water and relatively low amounts of said additional substance; said light oil fraction having the lowest density, wherein a second liquid fraction is a heavy solvent fraction rich in polar lipids said phase containing solvent, water and said additional substance, said heavy solvent fraction rich in polar lipids having the highest density, and wherein a first solid fraction is a solid fraction between the light oil fraction and the heavy solvent fraction, said solid fraction containing proteins and starch.

22. The method of claim 21, wherein an intermediate solvent fraction is formed, containing solvent, water and most of said additional substance, said intermediate fraction having an intermediate density.

23. The method of claim 21, separating the heavy solvent fraction rich in polar lipids from the other fractions and performing an additional fractionation step on the separated heavy solvent fraction, wherein solvent or water is added to the separated heavy solvent fraction in such a way that the concentration of solvent in the mixture is controlled to at least 50 wt %, where wt % is calculated on the total weight of solvent, water and additional substance, wherein said fraction separates into at least two fractions, wherein a first fraction is a heavier fraction rich in polar lipids and no or very small amounts of said additional substance, and wherein a second fraction is a lighter solvent fraction rich in solvent and said additional substance.

24. The method of claim 23, wherein said heavier fraction rich in polar lipids contains at least 25 lipid % polar lipids.

25. An oil rich in polar lipids, said oil comprising a mixture of a polar solvent comprising at least one carbon atom and water, wherein said oil contains at least 40 lipid % polar lipids as calculated on the total amount of lipids in said oil, wherein the total amount of polar solvent and water in said oil is between 20 and 30 wt %, wherein said polar lipids are obtained from fractionating an oil of biological material using a mixture of a polar solvent comprising at least one carbon atom, water and an additional substance selected from the group consisting of: mono-, di- and oligosaccharides comprising from 3 to 10 monosaccharide units, wherein said additional substance is present in an amount of at least 0.1 wt % calculated on the total weight of solvent, water and additional substance, to form at least two liquid fractions having different densities.

26. The oil of claim 25, wherein the polar solvent is ethanol, and the relationship in wt % between water and ethanol in said oil is between 30:70 and 50:50.

27. The oil of claim 25, wherein said oil is oat oil containing DGDG (digalactocyl diglyceride) with two fatty acids and DGDG with more than two fatty acids (estolides), wherein said oil contains more than 50% DGDG with more than two fatty acids (estolides) as calculated on the total amount of DGDG in said oil.

* * * * *

UNITED STATES PATENT AND TRADEMARK OFFICE
CERTIFICATE OF CORRECTION

| | |
|---|---|
| PATENT NO. | : 8,865,923 B2 |
| APPLICATION NO. | : 13/255869 |
| DATED | : October 21, 2014 |
| INVENTOR(S) | : Magnus Harrod |

It is certified that error appears in the above-identified patent and that said Letters Patent is hereby corrected as shown below:

On Title Page 2, Item (56) (Other Publications), line 1, please delete "Determinatin" and insert --Determination--, therefor;

In the Claims

Column 24, line 61 (approx.), please delete "(digalactocyl" and insert --(digalactosyl--, therefor.

Signed and Sealed this
Tenth Day of February, 2015

Michelle K. Lee
*Deputy Director of the United States Patent and Trademark Office*